United States Patent
Wieland et al.

(10) Patent No.: US 12,198,818 B2
(45) Date of Patent: Jan. 14, 2025

(54) AUTOMATED TREATMENT PROPOSAL

(71) Applicant: EXOCAD GMBH, Darmstadt (DE)

(72) Inventors: Christian Wieland, Darmstadt (DE); Paul Schnitzspan, Darmstadt (DE)

(73) Assignee: EXOCAD GMBH, Darmstadt (DE)

( * ) Notice: Subject to any disclaimer, the term of this patent is extended or adjusted under 35 U.S.C. 154(b) by 471 days.

(21) Appl. No.: 17/342,243

(22) Filed: Jun. 8, 2021

(65) Prior Publication Data
US 2022/0392645 A1 Dec. 8, 2022

(51) Int. Cl.
*G16H 50/50* (2018.01)
*A61C 9/00* (2006.01)
(Continued)

(52) U.S. Cl.
CPC ............. *G16H 50/50* (2018.01); *A61C 9/004* (2013.01); *A61C 13/34* (2013.01); *G06F 30/10* (2020.01);
(Continued)

(58) Field of Classification Search
CPC ........ G16H 50/50; G16H 20/40; G16H 40/20; G16H 30/20; G06F 30/10; A61C 9/004; A61C 13/34; A61C 9/00; G06T 19/20; G06T 2219/2004; G06T 2219/2016; G06T 2219/2021
See application file for complete search history.

(56) References Cited

U.S. PATENT DOCUMENTS 4,473,353 A * 9/1984 Greggs ................... A61C 5/20
433/215
5,338,198 A * 8/1994 Wu ...................... A61C 9/0053
433/213
(Continued)

FOREIGN PATENT DOCUMENTS

CA 2820539 A1 * 4/2009 ......... A61C 13/0004
CN 102054091 A * 5/2011 ............. A61C 7/002
(Continued)

OTHER PUBLICATIONS

Mariam Al-Abdallah, "Digital Method of Analyzing Three Dimensional Orthodontic Tooth Movement," 2008, University of Manchester, pp. 1-326. (Year: 2008).*

Primary Examiner — Kenneth Bartley
(74) Attorney, Agent, or Firm — PERRY + CURRIER INC.

(57) ABSTRACT

The invention relates to a computer system for providing a treatment proposal for a dentition of a patient. The computer system is configured to provide an current state model of the dentition and a target state model of the dentition; to provide a set of treatment options for treating the dentition, to check the provided treatment options, wherein the checking comprises determining whether the dentition of the patient is meeting the feasibility requirements assigned to the treatment option being checked; in case the dentition is determined to meet the feasibility requirements assigned to the treatment option being checked, to provide the treatment
(Continued)

proposal identifying the respective treatment option and implementation parameters determined for the measures of the identified treatment option for modifying the current state model such that one or more discrepancies of the current state model relative to the target state model are compensated.

21 Claims, 7 Drawing Sheets

(51) Int. Cl.
    *A61C 13/34*     (2006.01)
    *G06F 30/10*     (2020.01)
    *G06T 19/20*     (2011.01)
    *G16H 20/40*     (2018.01)
    *G16H 30/20*     (2018.01)
    *G16H 40/20*     (2018.01)

(52) U.S. Cl.
    CPC .............. *G06T 19/20* (2013.01); *G16H 20/40* (2018.01); *G16H 30/20* (2018.01); *G16H 40/20* (2018.01); *G06T 2219/2004* (2013.01); *G06T 2219/2016* (2013.01); *G06T 2219/2021* (2013.01)

(56) References Cited

U.S. PATENT DOCUMENTS

| | | | | |
|---|---|---|---|---|
| 5,431,562 | A * | 7/1995 | Andreiko | A61C 7/00 433/24 |
| 5,879,158 | A * | 3/1999 | Doyle | A61C 9/0053 433/24 |
| 6,099,314 | A * | 8/2000 | Kopelman | A61C 9/0053 433/213 |
| 6,217,325 | B1 * | 4/2001 | Chishti | B33Y 80/00 |
| 6,277,850 | B1 * | 8/2001 | Lubisch | C07D 403/04 514/249 |
| 6,632,089 | B2 * | 10/2003 | Rubbert | A61C 9/006 433/24 |
| 11,636,943 | B2 * | 4/2023 | Kopelman | G16H 30/40 703/1 |
| 11,654,001 | B2 * | 5/2023 | Roschin | G16H 50/50 433/214 |
| 2002/0015934 | A1 * | 2/2002 | Rubbert | A61C 7/146 433/29 |
| 2004/0015327 | A1 * | 1/2004 | Sachdeva | A61C 7/00 702/167 |
| 2004/0197727 | A1 * | 10/2004 | Sachdeva | A61C 7/00 433/24 |
| 2005/0271996 | A1 * | 12/2005 | Sporbert | A61C 7/00 433/24 |
| 2010/0138025 | A1 * | 6/2010 | Morton | A61C 7/00 700/103 |
| 2014/0379356 | A1 * | 12/2014 | Sachdeva | A61C 7/002 705/2 |
| 2016/0015488 | A1 * | 1/2016 | Miltau | A61C 9/004 433/196 |
| 2018/0263733 | A1 * | 9/2018 | Pokotilov | A61C 7/002 |
| 2019/0175303 | A1 * | 6/2019 | Akopov | A61C 7/002 |
| 2019/0333622 | A1 | 10/2019 | Levin et al. | |
| 2020/0405445 | A1 * | 12/2020 | Tsai | A61C 7/08 |
| 2021/0059796 | A1 * | 3/2021 | Weiss | G06N 3/047 |
| 2021/0073998 | A1 | 3/2021 | Brown et al. | |
| 2021/0074061 | A1 * | 3/2021 | Brown | G06T 17/205 |
| 2022/0028532 | A1 * | 1/2022 | Kopelman | G16H 30/20 |

FOREIGN PATENT DOCUMENTS

| | | | | |
|---|---|---|---|---|
| CN | 101977564 | B * | 3/2019 | ............ A61B 6/032 |
| DE | 102019003296 | A1 * | 11/2019 | |
| KR | 20210002693 | A * | 1/2021 | |
| WO | WO-0180761 | A2 * | 11/2001 | ........ A61C 13/0004 |
| WO | WO-2009048475 | A1 * | 4/2009 | ........ A61C 13/0004 |
| WO | WO-2022114709 | A1 * | 6/2022 | |

* cited by examiner

AUTOMATED TREATMENT PROPOSAL

FIELD

The invention relates to the field of dental technology. More particularly, the invention relates to a computer system for providing a treatment proposal for a dentition of a patient. The invention furthermore relates to a computer program product as well as a computer-implemented method for providing a treatment proposal for a dentition of a patient.

BACKGROUND

For treating a dentition of a patient in order to modify the dentition for varies purposes, e.g., to improve an aesthetic appearance of a smile of a patient, there may be different treatment options. Finding a suitable treatment option may be complex and laborious. In case a treatment option is chosen, which later on turns out to be unsuitable, either the result of the modification may be unsuitable and/or only short living or an alternative treatment option may have to be found. Finding a treatment option may further increase, e.g., double, the complexity and amount of labor required.

SUMMARY

It is an objective to provide for a computer system, a computer program product and a computer-implemented method for providing a treatment proposal for a dentition of a patient.

In one aspect, the invention relates to a computer system for providing a treatment proposal for a dentition of a patient. The computer system comprises a processor and a memory storing program instructions executable by the processor. Execution of the program instructions by the processor causes the computer system to provide a 3D digital model of a current state of the dentition as a current state model using scan data of the dentition. Furthermore, a 3D digital model of a target state of the dentition to be achieved as a target state model is provided. The target state model is generated using the current state model. A set of treatment options for treating the dentition is provided. Each of the treatment options define one or more pre-defined measures of dentition modifications. Each of the treatment options are assigned with a set of one or more feasibility requirements to be met by the dentition for the treatment option to be feasible. One or more of the provided treatment options are checked. The checking comprises determining, whether the dentition of the patient is meeting the feasibility requirements assigned to the treatment option being checked using the current state model. In case the dentition is determined to meet the feasibility requirements assigned to the treatment option being checked, the treatment proposal is provided. The treatment proposal identifies the respective treatment option and implementation parameters determined for the measures of the identified treatment option. The implementation parameters are determined for modifying the current state model such that one or more discrepancies of the current state model relative to the target state model are compensated.

For example, the computer system may provide automatic treatment selection automatically selecting a treatment option for a dental treatment, e.g., reconstruction. The automatically selected treatment option may be provided as a treatment proposal. The treatment options of the set of treatment options may, e.g., be treatment options for improving the aesthetic appearance of a smile of a patient.

Different treatment options may be checked. If a check is positive for one of the treatment options, a recommendation in form of a treatment proposal recommending the respective treatment option may be issued. The treatment proposal may, e.g., be outputted via a user interface of the computer. For example, the treatment proposal may be displayed on a display of the computer system using a graphical user interface. The check may be positive, in case the treatment option checked is determined to be feasible in view of the current state of the dentition to be treated. A treatment option is feasible, if the dentition is meeting the feasibility requirements required to be met for the respective treatment option. Thus, an automated recommendation for a dental treatment may be provided.

The treatment options may, e.g., be ordered according to a ranking order. For example, the treatment options may be checked subsequently following the ranking order, until the dentition is determined to meet the feasibility requirements assigned to the treatment option being checked. When feasibility requirements of a treatment option being checked are met, the checking may, e.g., be terminated and the respective treatment option may be provided in form of a treatment proposal as a recommendation. The checking may, e.g., be interrupted and waiting for a response to the treatment proposal provided. In case an acceptance command accepting the treatment proposal is received from a user, e.g., via a user interface, the checking is terminated. In case a rejection command rejecting the treatment proposal is received from a user, e.g., via a user interface, the checking may be continued with the next treatment option in line according to the ranking order. Alternatively, all the treatment options may be checked and treatment proposal may comprise all the feasible treatment options of the set of treatment options being checked. The feasible treatment options may be provided, e.g., displayed, indicating their ranking order. Thus, a user may be enabled to select one of the feasible treatment options, e.g., taking into account their ranking.

The checking may take into account additional information being provided with regard of the dentition of the patient. This additional information may for example be provided in form of additional scan data. The additional scan data may provide information regarding external and/or internal structures of the teeth. The additional information may be indicative of one or more contraindications of the dentition regarding one or more of the treatments options. In case there is a contraindication, like a tooth damage, excluding a usage of a particular treatment option per se, the dentition may be determined not to meet the feasibility requirements of the respective treatment option without requiring a further analysis, e.g., using implementation parameters of the respective treatment option.

The checking may, e.g., take into account implementation parameters for the measures of the treatment option being checked. The checking may, e.g., comprise determining implementation parameters for the measures of the treatment option being checked for modifying the current state model such that one or more discrepancies of the current state model relative to the target state model being compensated. Using the implementation parameters, it may be determined which preparations of the dentition are required for implementing the measures of a treatment option being checked. Determining whether the dentition is meeting the feasibility requirements may comprise determining whether the dentition allows to implement the respective measures according to the implementation parameters. For example, if implementing a crown requires removal of a tooth tissue, it may be determined whether the tooth tissue is removable without risking to significantly damage the respective tooth, e.g., by damaging the pulp of the tooth. Furthermore, determining whether the dentition is meeting the feasibility requirements may comprise determining whether the dentition with the measures according to the implementation parameters implemented is meeting the feasibility requirements. For example, if implementing a crown requires removal of a tooth tissue, it may be determined whether the respective tooth after the removal of the tooth tissue provides sufficient support for the crown.

The scan data of the dentition for providing the current state model may be acquired by using a scanner, e.g., an optical scanner. The scan may be a direct scan of the patient's dentition, e.g., an intraoral scan. Alternatively or additionally, an indirect scan of the patient's dentition may be used to acquire the scan data. For example, a dental impression of the patient's dentition or a dental model of the dentition, like a plaster model, may be scanned.

A current state model, i.e., a digital 3D model of a current state of the dentition is provided. This current state model may be generated using the scan data of a direct and/or indirect scan of the dentition. The current state model resembles an actual state of the patient's dentition, i.e., it may be a digital replica of the physical dentition. The current state model may, in particular, resemble the geometrical form of the physical dentition. The current state model may be generated by the computer system or it may be received from an external source. The external source may, e.g., be a server, like a cloud server, providing the current state model via a network. The external source may, e.g., be a removable storage device providing the current state model via a direct communication connection.

Furthermore, a digital 3D model of a target state of the dentition is provided. This model is referred to as a target state model. The target state model may be resembling a digital replica of a physical state of the patient's dentition to be achieved by dental treatment. The target state model may be generated using the current state model. For this purpose, the current state model may be digital modified until it resembles an intended state of the dentition. The modification may, e.g., comprise removing, replacing, resizing, reshaping, reorienting, repositioning one or more digital teeth comprised by the current state model and/or adding one or more digital teeth, e.g., library teeth. For example, one or more digital teeth of the current state model may be replaced by one or more digital teeth from a tooth library. Furthermore, one or more of the library teeth may be adjusted. The adjustments may comprise, e.g., resizing, reshaping, reorienting and/or repositioning. The target state model may be generated by the computer system or it may be received from an external source. The external source may, e.g., be a server, like a cloud server, providing the target state model via a network. The external source may, e.g., be a removable storage providing the target state model via a direct communication connection.

A set of possible treatment options for treating the dentition is provided. The set of possible treatment options comprises a plurality of treatment options. Each of the treatment options defines one or more pre-defined measures of dentition modifications. Each of the treatment options is assigned with a set of one or more feasibility requirements to be met by the dentition for the treatment option to be feasible. For example, the possible treatment options are alternative treatment option. Thus, each of these treatment options provides one or more measures for modifying a dentition. Each of these treatment options may provide one or more measures for modifying the current state of the dentition according to the current state model such that one or more differences between the current state of the dentition and the target state of the dentition defined by the target state model are reduced. For example, one or more of these treatment options provide treatment options for transferring the current state of the dentition into the target state of the dentition, i.e., to modify the current state such that the result of the modification matches the target state. For example, all of these treatment options provide treatment options for transferring the current state into the target state.

The set of treatment options may, e.g., comprise the treatment option of using one or more veneers. A veneer is a layer of material, e.g., a shell-like layer, which is placed on a tooth. A veneer may be used to partially and/or fully cover a facial surface of a tooth, in particular a labial surface of a tooth. A veneer may be a laminate veneer provided in form of a thin layer only covering the respective the surface, e.g., labial surface of the tooth. Veneers may improve an aesthetic appearance of teeth and thus an aesthetic appearance of a smile of a patient. Furthermore, a veneer may protect a tooth's surface, on which the veneer is placed, from damage.

A veneer may for example be made using a composite, also referred to as dental composite resins. Such dental composite resins are dental cements made of synthetic resins. A dental composite may, e.g., comprise a resin-based oligomer matrix, such as a bisphenol A-glycidyl methacrylate (BISGMA), urethane dimethacrylate (UDMA) or semi-crystalline polyceram (PEX), as well as an inorganic filler such as silicon dioxide (silica). Dental compositions may vary widely. For example, proprietary mixes of resins may be used for forming the matrix as well as engineered inorganic filler may be used, such as filler glasses and/or glass ceramics.

The filler may be used to increase strength of the composite, increase wear resistance, decrease polymerization shrinkage, increase translucency, increase fluorescence, adjust color, and/or reduce exothermic reaction on polymerization. Glass fillers may, e.g., improve optical and mechanical properties of a dental composite. Ceramic fillers may, e.g., include zirconia-silica and zirconium oxide. A coupling agent such as silane may be used to enhance the bond between matrix and filler. An initiator, such as camphorquinone (CQ), phenylpropanedione (PPD) or lucirin (TPO), may be used to initiate the polymerization reaction of the resins, e.g., when blue light is applied. Furthermore, various additives may be used to control the rate of the polymerization reaction.

Resin fillers may, e.g., be made of glasses or ceramics. Glass fillers may, e.g., be made of crystalline silica, silicone dioxide, lithium/barium-aluminum glass, and/or borosilicate glass containing zinc/strontium/lithium. Ceramic fillers, e.g., made of zirconia-silica, or zirconium oxide. Fillers may, e.g., comprise macrofilled fillers with particle sizes, e.g., in the range of 5-10 μm, microfilled fillers with particle sizes of less than 5 m, e.g., 0.4 am, hybrid fillers with particles of various sizes and a filler load of, e.g., 75-85% by weight, nanofilled fillers with particle sizes, e.g., in the range of 20-70 nm, or bulk fillers with nanohybrid particles, like non-agglomerated silica and zirconia particles, and a filler load of, e.g., 77% by weight.

A composite veneer may be a direct veneer directly built-up in the mouth or an indirect veneer fabricated outside of the mouth and bonded in the mouth to a tooth using an adhesive, e.g., a resin cement.

A veneer may for example be made using a dental porcelain, also referred to as dental ceramic. The ceramic may, e.g., be ceramic of composition category 1, i.e., a glass-based system, like, e.g., feldspathic porcelain; ceramic of composition category 2, i.e., a glass-based system with filler, e.g., crystalline like leucite or lithium disilicate; ceramic of composition category 3, i.e., a crystalline-based system with glass fillers, e.g., alumina; ceramics of composition category 4, i.e., polycrystalline solids, like alumina and/or zirconia. The crystalline phase of crystalline ceramics may, e.g., comprise leucite, leucite and fluorapatite, lithium disilicate, alumina, spinel, alumina-zirconia (12Ce-TZP), zirconia (3Y-TZP), zirconia/fluorapatite-leucite glass-ceramic, or sanidine. A manufacturing technique of manufacturing crystalline ceramics may, e.g., comprise sintering, heat-pressing, sintering and heat-pressing, dry pressing and sintering, slip-casting and glass infiltration, soft machining, soft machining and glass-infiltration, soft machining and sintering, hard machining, or hard machining and heat treatment.

A porcelain veneer may be an indirect veneer fabricated outside of the mouth and bonded in the mouth to a tooth using an adhesive, e.g., a resin cement.

A veneer may be used to adjust the color of discolored tooth, to modify the shape of a malformed, malpositioned or worn tooth, to cover unaesthetic features of a tooth caused, e.g., by enamel hypoplasia, enamel hypocalcification, fluorosis, enamel fractures and/or enamel loss by erosion. For example, veneers may be used to close free spaces between teeth, e.g., due to a small size of the teeth, which may not easily be closed by orthodontics. Furthermore, veneers may be used to lengthen teeth that have been shortened by wear, to fill triangles between teeth caused by gum recession, to provide a uniform color of the teeth, a uniform shape of the teeth, and/or uniform symmetry of the teeth, and/or make the teeth appear straight. Veneers may thus, e.g., be used to improve the aesthetic appearance of teeth with worn away edges, malformed teeth, malpositioned teeth and/or teeth that appear crooked. Applying a veneer, e.g., minimal to no tooth preparation may be required.

The veneers may be manufactured using methods of CAD/CAM dentistry.

The set of treatment options may, e.g., comprise the treatment option of using one or more dental crowns. A crown, also referred to as a dental cap, is a type of dental restoration which completely caps or encircles a tooth. A crown may, e.g., be bonded to the tooth by dental cement. Crowns may be made from many materials and, e.g., be fabricated using an indirect method, i.e., be fabricated outside of the mouth. A crown may be used to improve the strength, improve the aesthetic appearance of teeth and/or to halt deterioration of a tooth.

The crown may, e.g., be an inlay, onlay or single-unit crown. The crown may, e.g., be a full crown. The crown may, e.g., be a ceramic crown or a metal-ceramic crown. Ceramic crowns may be made using dental ceramics. Dental ceramics may, e.g., comprise silica, alumina and/or zirconia. Metal-ceramic crowns are hybrids of metal and ceramic crowns. The metal part may, e.g., be made of a base metal alloy, also referred to as a bonding alloy. Exemplary base-metal alloys may be silver-palladium, silver-palladium-copper, nickel-chromium, nickel-chromium-beryllium, cobalt-chromium, or titanium. To obtain an aesthetic finish a ceramic may be bonded to a metal framework provided by the base metal analogy. The bonding may, e.g., be implemented by a compression fit, e.g., via ceramic shrinkage on firing, by a micro-mechanical retention, e.g., via surface irregularities, or a chemical union, e.g., via oxide formation.

The crowns may be manufactured using methods of CAD/CAM dentistry.

Using CAD/CAM methods a 3D model of the crown may be generated. Design information defining the 3D geometry of the crown may be used to control a manufacturing device, like a milling device. The milling device may use one or more milling tools, e.g., tungsten carbide or diamond burs, to mill the restoration, i.e., the crown, from a blank. The blank may be made of a material, e.g., ceramic, with a pre-determined shade to match a target color. The crown may be sectioned from the remainder of the unmilled blank and tried in the patient's mouth. If the crown fits well, it may be cemented on the prepared tooth.

In order to provide a sufficient retention and resistance to hold the crown in place, the respective tooth or tooth stump intended to receive the crown may have to be prepared. In this context, retention refers to a resistance of movement of a restoration, i.e., crown, along a path of insertion or along a long axis of the tooth being prepared. Resistance refers to a resistance of movement against forces applied apically or in an oblique direction preventing movement under occlusal forces. Retention may be determined by a relationship between opposing surfaces of the preparation, e.g., a relationship of buccal and lingual walls of the preparation.

For full coverage crown, the form of a tooth or tooth stump may be prepared to slightly taper, i.e., converge in an occlusal direction. This may, e.g., allow to prevent undercuts, compensate for crown fabrication inaccuracies as well as for excess cement to escape in order to optimize a seating of the crown on the preparation. For example, axial walls may, e.g., be prepared with a 2-3° taper on each wall and an overall 4-6° taper. In order to ensure a sufficient retention, taper be kept to a minimum whilst eliminating undercuts.

The occluso-gingival length or height of a preparation may affect resistance as well as retention. In order to provide a sufficiently large surface, a tall preparation may be desirable. To ensure sufficient retention for a crown, a length of the preparation may be greater than a height formed by an arc of a cast pivoting around a point on a margin on an opposite side of the restoration. The arc may be affected by a diameter of the tooth prepared. Therefore, the smaller the diameter, the shorter the length of the crown may have to be, in order to provide a sufficient retention. Retention may, e.g., be improved by placing grooves in the axial walls.

Retention may further be improved by geometrically limiting a number of paths along which the crown is removable the preparation.

Removal of healthy tooth tissue, when preparing a tooth or tooth stump, may be minimized as far as possible.

The crown may be required to comprise enough material to withstand normal masticatory function. On the other hand, the crown has to be contained within a space created by the tooth preparation. Depending on the material used to manufacture the crown, sufficient occlusal and axial reductions of a tooth is required to house the crown.

Metal-ceramic crowns and full ceramic crowns may, e.g., require an occlusal clearance, e.g., a clearance of 2.0 mm. The occlusal clearance may follow the natural outline of the tooth in order to ensure a sufficient thickness of the crown over the complete occlusal section. For example, it may be required that the chewing portion of the crown is 1.5 mm thick or greater.

An axial reduction of the prepared tooth may be required to allow for a sufficient lateral thickness of the crown in dependence of the material chosen. Depending on the type of crown to be fitted, there may be a minimum preparation thickness. A metal-ceramic or full ceramic crown may, e.g., require at least 1.2 mm.

Preparing a tooth for a crown may therefore require a more extensive removal of tooth tissue compared to a preparation for using a veneer.

The set of treatment options may, e.g., comprise the treatment option of replacing a tooth or tooth stump by a dental prosthesis. For example, a missing tooth may be replaced. For example, an existing tooth or remaining tooth part may be replaced. The replacement of an existing tooth or tooth part comprise an extraction of the respective tooth or tooth part.

The set of treatment options may, e.g., comprise the treatment option of using orthodontics. Orthodontics refers to the correction of malpositioned teeth and jaws as well as misaligned bite patterns. Using orthodontics position and/or orientation of teeth may be modified. Orthodontic measures may comprise using one or more of the following orthodontic treatment appliances: dental braces, lingual braces, clear aligners or palatal expanders.

Dental braces may be used for aligning and straightening teeth and for helping position them with regard to a person's bite. Braces may further be used to fix gaps. They may be used to correct underbites, as well as malocclusions, overbites, open bites, deep bites, cross bites, crooked teeth. Braces can be either cosmetic or structural.

Using braces, teeth as moved over time by a constant force and pressure applied on the teeth. Braces may, e.g., comprise: brackets, bonding material, an archwire, and ligature elastics. The teeth are moved, when the archwire puts pressure on the brackets attached to the teeth by the bonding material. Ligature elastics may be used to keep the archwire held in place, e.g., a slot on the bracket. Additional springs and/or rubber bands may be used to put additional force in a specific direction.

Lingual braces are braces with orthodontic brackets attached on the inner, i.e., lingual side of the teeth.

Clear aligners are orthodontic devices in form of transparent, plastic form of dental braces used to adjust teeth. A computerized model may be used for defining a plurality of stages between teeth positions as well as orientations of the current state and teeth positions as well as orientations of the target state. A clear aligner may be created for each stage. These clear aligners may be used successively in order to transform the teeth positions as well as orientations of the current state into the teeth positions as well as orientations of the target state.

A palatal expander is an orthodontic device used to widen the upper jaw (maxilla), e.g., so that the bottom and upper teeth may fit together better. A widening may also be used to gain room for teeth in cases of a moderate crowding of the teeth in the upper jaw.

For example, discrepancies between the current state of the dentition and the target state of the dentition may be determined. The discrepancies between the current state of the dentition and the target state of the dentition may be determined by a comparison of the current state model and the target state model. The discrepancies may, e.g., comprise geometrical discrepancies and/or color discrepancies. Geometrical discrepancies may comprise discrepancies regarding position, orientation, size and/or shape of teeth. The discrepancies may be used to determine, where treatment measures are required. For example, the discrepancies may be used to determine which teeth of the dentition have to be modified.

The discrepancies may be used to determine implementation parameters for an implementation of the pre-defined measures such that one or more discrepancies of the current state model relative to the target state model are compensated. For example, implementation parameters for the implementation of the pre-defined measures may be determined such that one or more discrepancies of the current state model relative to the target state model are compensated.

The implementation parameters may for example be determined depending on the target state model. For this purpose, implementation of the pre-defined measures may be determined such that they match the target state model. For example, the target model may define the margin within which the measures of the treatment options, like veneers or crowns, have to be implemented. For example, a veneer may be configured such that it matches the lingual appearance of a tooth of the target state model. The configured veneer may be used to determine, whether and/or how an existing tooth of the current state model has to be prepared in order to provide a suitable support surface for the respective veneer. For example, a crown may be configured such that it matches the crown of a tooth of the target state model. The configured crown may be used to determine, how an existing tooth of the current state model has to be prepared in order to provide a tooth stump with a suitable support for the respective crown.

The implementation parameters may, e.g., define preparation requirements defining how teeth of the current state model have to be prepared for implementing the measures of a treatment option. Preparation requirements for teeth of the current state model may, e.g., be determined by a subtraction of the configured measures, like veneers or crowns. The configured measures may, e.g., be subtracted from the current state model registered with the target state model used to configure the measures. The configured measures may, e.g., be subtracted from the target state model registered with the current state model and the resulting reduced target state model may be subtracted from the current state model. Using these preparation requirements provided as a part of the implementation parameters, the treatment proposal may further comprise preparation instruction for the current state model, in order to prepare the current state model for the respective treatment measures of the respective treatment proposal.

For example, the method may comprise providing two, e.g., 2D photographs of the patient. A first one of the photographs may be a smile photograph. The smile photograph may be a photograph of a smile of a patient, e.g., depicting the smiling patient. A second one of the photographs may be a "retracted" photograph, in which the patient's lips are retracted or pushed back with the help of a plastic mouthpiece, e.g., a transparent mouthpiece, to reveal the teeth of the patient as much as possible.

The photographs may be registered with the current state model, i.e., with a 3D scan of the patient's dentition. The registration may for example use a point registration or an automatic registration using machine learning may be implemented. For example, the retracted photograph depicting more of the patient's teeth than the smile photograph may be used to register the 3D current state model of the dentition with the 2D photographs of the teeth. The retracted photograph and the smile photograph may be registered with each other, e.g., using the parts of the teeth shown on both photographs. The smile photograph may be placed lingual in front of the current state model with the smile being cut out along the lip lines such that in the mouth of the patient the teeth of the 3D model are visible instead of the cut-out teeth depicted in the smile photograph. For placing the smile photograph in front of the current state model, the registration of the smile photograph with the retracted photograph may be used. Alternatively, only the smile photograph may be used and registered with the current state model before cutting out the teeth, in case the teeth sections shown in the smile photograph are sufficient for a registration.

This placement of the smile photograph in front of the current state model may allow to see the current state model through the cut-out in the smile photograph. The current state model may be modified in order to provide the target state model. Replacing the current state model by the target state model and vice versa, the effects of the modifications of the current state model resulting in the target state model may be illustrated in context of the 2D smile photograph. Thus, a realistic impression of the aesthetic appears of possible 3D modifications of the patient dentition may be provided in the 2D photograph. In particular, the effects of such modifications on the aesthetic appearance of the patient's smile may be illustrated.

For example, a tooth library may be used providing library teeth, i.e., pre-defined 3D digital tooth models, allowing for a realistic rendering of the tooth colors of the patient, e.g., using the photographs.

The target model may, e.g., be generated using library teeth from the tooth library. For example, one or more teeth of the patient as defined by the current state model may be replaced by a tooth from the tooth library. The current state model behind the smile photograph may be replaced by the resulting target state model. Thus, the result of the modifications of the current state model and their effects on the smile of the patient, in particular on the aesthetic appearance of the smile, may be determined immediately and may, e.g., be presented to the patient. Thus, a realistic impression of the potential results of a treatment of the patient's dentition on the patient's smile, in particular on its aesthetic appearances, may be illustrated.

After generating a satisfying target state model and, e.g., checking the aesthetic effect of the respective target state model on the smile of the patient, a treatment proposal for the dentition of the patient in order to achieve the target model may be provided. For this purpose, the set of treatment options for treating the dentition may be checked.

For example, in case the result of applying the treatment according to the treatment proposal to the current state model differs from the target state model, a modified target model may be generated showing the result of the applying the treatment according to the treatment proposal. Furthermore, the aesthetic effect of the respective modified target state model on the smile of the patient may be checked. For this purpose, the target state model behind the smile photograph may be replaced by the modified target state model. Thus, the result of the modifications of the current state model according to the treatment proposal and their effects on the smile of the patient, in particular on the aesthetic appearance of the smile, may be determined and may, e.g., be presented to the patient. Thus, a realistic impression of the potential results of a treatment of the patient's dentition according to the treatment proposal on the patient's smile, in particular on its aesthetic appearances, may be illustrated.

By checking feasibility requirements, when selecting a treatment proposal, it may be ensured that the proposed treatment option is actually feasible. Thus, before applying a treatment, the risk of surprising obstacles arising during application may be reduced or minimized. Otherwise, such obstacles may, e.g., result in an insufficient result of the treatment.

Thus, it may be avoided that in the process of designing, e.g., a veneer, it is determined that the veneer cannot be implemented, e.g., due to a violation of minimum thicknesses of the veneer or because a bonding surface is too small. The dentition may, e.g., only allow for a veneer which is too thin and/or provides a bonding surface is too small. For example, in case of a crown designed using a library tooth, it may be avoided to determine during designing the crown using the library tooth that the respective crown cannot be designed with the desired result on the available preparation. For example, the dentition may only allow for preparations, which are incompatible with the intended and/or required design of the crown.

Furthermore, it may be avoided that a more invasive treatment option is applied, even though a less invasive may be possible in order to achieve the same or an equivalent result, in particular the same or an equivalent aesthetic effect on the smile of a patient. More invasive may, e.g., refer to a larger loss of natural tooth tissue. For example, it may be avoided that a crown is prepared, e.g., because of uncertainties whether a veneer may be possible, although a veneer would actually be possible. Preparing a crown, even though a veneer is possible, may lead to unnecessarily losses of healthy teeth tissue or even complete healthy teeth by the patient. This may be avoided by using the feasibility check. Based on the feasibility check, it may be determined, whether, e.g., veneers are actually a feasible treatment option for the dentition of the individual patient. For example, only in case veneers are no feasible treatment option, crowns or a complete replacement of teeth, e.g., using implants, may be checked.

Furthermore, it may be avoided that a prosthesis, like a crown, is prepared, even though it is not feasible. For example, a crown may not fit. For example, e.g., minimum thicknesses may not be met due to insufficient space. The crown may be adjusted with a wall thickness below a required minimum thickness, which may result in a breaking of the crown after a short period of time.

Furthermore, it may be avoided that a first treatment option is applied, which turns out to be infeasible or to provide an insufficient result, such that several different treatment options may have to be applied before a feasible and satisfying result is reached.

The decision of which treatment option to choose may be facilitated by providing a treatment proposal based on a check of feasibility requirements. Furthermore, the treatment proposal may comprise instructions, e.g., based on the implementation parameters, as how exactly the patient's teeth is to be prepared for the treatment option proposed.

The target model may, e.g., be generated replacing teeth of the current state model by teeth from a tooth library. The teeth of the current state model may be segmented at the position, where the desired library teeth are placed. The teeth may, e.g., be segmented automatically or semi-automatically. The segmentation of the teeth of the current state model may enable a digital tooth extraction. A digital 3D model of a library tooth may be placed and adjusted at the position of the extracted tooth. The library tooth may define a margin in which the preparation of the original tooth of the current state model may take place. The current state model may, e.g., be presented via a user interface in a transparent form, overlaid over the target state model being generated, e.g., by replacing original teeth with library teeth.

For checking a treatment option comprising usage of a prosthesis, like a veneer or crown, as a treatment measure, a provisional version of the prosthesis may be generated and used for the checking. This provisional prosthesis may be generated in minimal form, i.e., such that the preparation of the natural tooth in order to apply the prosthesis is kept minimal. For example, a veneer may be generated. A library tooth of the target model, to which the veneer is to be applied, may be adapted to a bottom of the provisional veneer. It may be checked, whether the feasibility requirements are met. In case a veneer is not feasible, e.g., a crown may be checked. For the crown as well a provisional may be generated within the margin defined by the library tooth and the library tooth may be adapted to a bottom, i.e., clearance, of the respective provisional. Again, the feasibility requirements may be checked. In case, a crown in infeasible, a tooth extraction may be checked as a further treatment option. If a tooth extraction and replacement using an implant is infeasible, e.g., alternatives may be checked. For example, using orthodontics may be checked as an alternative.

For a crown, it may be required that a prepared tooth stump, on which the crown is to be placed, does not become too thin and/or pointed. The respective tooth stump may, e.g., be represented by the adapted library tooth. For example, a ball with a diameter resembling a required minimum diameter of the tooth stump may be placed within a clearance of the 3D digital model of the crown. The clearance is intended for receiving the respective tooth stump. It may be checked that the ball does not or only within pre-defined limits penetrate an inner surface of the 3D digital model of the crown defining the clearance.

Furthermore, in order to check a minimum thickness of a veneer or a crown, a distance between an outer surface of the veneer or crown opposing a bonding surface of the veneer or crown may be measured. In case the minimum thickness requirement is violated, the veneer or crown may be regenerated with a larger thickness. In this case, it may, e.g., have to be checked again, whether a prepared tooth stump still has a sufficiently large diameter.

The generated prosthesis, e.g., veneer or crown, may be subtracted from the current state model in order to define a preparation of the current state model required for implementing the respective treatment option.

The treatment proposal may provide the implementation parameters as part of a description describing how to prepare the current state model for applying the proposed treatment option. Guiding instructions may be providing, identifying where tooth tissue has to be removed to which extend in order to prepare the current state of the dentition for applying the proposed treatment option.

For example, one or more of the feasibility requirements depend on the implementation parameters of the measures of the treatment option. The determining whether the dentition of the patient is meeting the feasibility requirements assigned to the treatment option being checked may be further based on the implementation parameters determined for the treatment option being checked.

The implementation parameters determined for the measures of a treatment option may define which modifications of the current state model are required in order to execute the respective treatment option. For example, the implementation parameters may define how much healthy tooth tissue has to be removed in order to provide a sufficient support surface for the veneer. For example, the implementation parameters may define how much healthy tooth tissue has to be removed in order to provide a preparation of a tooth suitable to support a ground. In case of a tooth extraction and replacement of the respective tooth by an implant, the implementation parameters may define the extraction of the respective tooth. It may be checked whether the current state model allows for the required modifications. If the current state model and thus the dentition does not allow for the required modifications, the feasibility requirements may not been meet.

For example, feasibility requirements may depend on implementation parameters, if the implementation parameters define a support for a measure of a respective treatment option, e.g., veneer or ground. The feasibility requirements may comprise requirements to be met by a respective support. Thus, the implementation parameters determined may be checked as well in order to ensure that the respective implementation parameters are not in conflict with feasibility requirements of the respective treatment option.

For example, the providing of the current state model comprises generating the current state model using the scan data.

The current state model may, e.g., be generated using scan data acquired by an intraoral scan of the dentition of the patient. The intraoral scan may for example be an optical scan. Alternatively, the scan data may be acquired by scanning an impression of the dentition of the patient. The impression may for example be scanned using an optical sensor. In addition, scan data may, e.g., be used, which is acquired in the near-infrared range using near-infrared imaging (NIRI). NIRI uses electromagnetic radiation e near-infrared region of the electromagnetic spectrum to scan an internal structure, i.e., enamel and dentine, of patients' teeth. Tooth enamel is transparent to near-infrared wavelengths, while tooth dentin and other interference, e.g., caries, may show up as visual contrast. Thus, by scanning the internal structure using NIRI, interproximal caries detection may be detected.

In addition, scan data may be used, which is acquired using an X-ray of the patient's dentition. For example, the scan data may be acquired using a panoramic radiograph, i.e., a panoramic scanning dental X-ray of the upper and lower jaw. A panoramic radiograph provides a panoramic image showing a two-dimensional view of a half-circle from ear to ear.

In addition, scan data may be used, which is acquired using a CT scan, i.e., a computer tomography scan. A CT scan provides computer-processed combinations of multiple X-ray measurements taken from different angles to produce tomographic, i.e., cross-sectional images. For example, a focal plane tomography may be used with images of multiple planes being taken to generate a composite panoramic image.

For example, scan data acquired using cone-beam computed tomography (CBCT), also referred to as digital volume tomography (DVT), may be used. CBCT consisting of X-ray computed tomography with divergent X-rays forming a cone.

Additional scan data, e.g., acquired using nearfield-infrared imaging, X-ray imaging, and/or CT scanning, may have a beneficial effect of providing additional information about inner structures of the dentition, in particular about the inner structures of the teeth.

Also other types of scan data acquired using further imaging methods of oral and maxillofacial radiology (OMFR), also referred to as dental and maxillofacial radiology (DMFR), may be used providing additional insight in the patient's craniofacial, dental and adjacent structures. The further imaging methods may, e.g., comprise multi-slice CT, magnetic resonance imaging (MRI), positron emission tomography (PET), ultrasound, cephalometric imaging, intra-oral imaging, e.g., bitewing, periapical and occlusal radiographs, as well as special methods, like sialography.

For example, the providing of the current state model comprises acquiring the scan data.

The computer system may for example comprise a scanning device, i.e., scanner for acquiring the respective scan data, or be part of a system comprising the respective scanning device. The scanning device may for example be an optical scanner configured for an intraoral scan of the dentition of the patient. The scanning device may be an optical scanner configured for scanning an impression of the dentition of the patient. The scanning device may for example be a near-infrared scanner configured for near-infrared imaging of the dentition of the patient. The scanning device may for example be an X-ray scanner configured to acquire X-ray images, in particular X-ray panorama images, of the patient's dentition. The scanning device may for example be a CT scanner, in particular a CBCT scanner, configured for acquiring CT data of the patient's dentition and to reconstructing CT images using the acquired CT data.

For example, the providing of the target state model comprises generating the target state model using the current state model. The target state model may be generated using the current state model by modifying the position and/or orientation of one or more teeth of the current state model. The generating of the target state model may comprise modifying the shape and/or dimension of teeth comprised by the current state model. The generating of the target state model may comprise replacing one or more teeth of the current state model by teeth from a tooth library. For modifying the current state model, teeth which are modified or replaced may be segmented. The segmentation of individual teeth may be executed automatically or semi-automatically.

For example, the generating of the target state model comprises replacing one or more 3D digital models of actual teeth or tooth stumps comprised by the current state model with one or more 3D digital models of teeth from a tooth library.

Replacing actual teeth or tooth stumps by 3D digital models of teeth from a tooth library may have the beneficial effect that 3D digital models may be selected from the tooth library, which in view of their shape and/or color match teeth of the dentition of the patient. Furthermore, the respective 3D digital models may already be optimized regarding their aesthetic appearance, like shape, symmetry and/or color. The respective 3D digital models may only have to be adjusted regarding their position, orientation and/or size.

For example, the generating of the target state model comprises modifying one or more features of the following features of one or more 3D digital models of actual teeth or tooth stumps comprised by the current state model: shape, size, position, orientation.

By adjusting the shape, size, position and/or orientation of a tooth comprised by the current state model, the respective tooth may be optimized in order to match a desired target state. For example, the aesthetic appearance of the respective tooth may be improved, e.g., optimized.

For example, the set of treatment options comprises one or more of the following treatment options using dental prostheses: using one or more veneers to be arranged on one or more teeth of the dentition as measures of dentition modifications; using one or more crowns to be arranged on one or more teeth or tooth stumps of the dentition as measures of dentition modifications, the crowns; replacing one or more teeth or tooth stumps of the dentition as measures of dentition modification. The replacing comprises extracting one or more teeth from the dentition and inserting one or more dental implants configured for supporting a crown or a bridge. Furthermore, the respective treatment option may comprise providing and implement the crown or bridge using the one or more dental implants.

For example, the implementation parameters for one or more of the measures of the treatment options comprise determining one or more of the following: the size of the dental prostheses to be used, the shape of the dental prostheses to be used.

Determining the implementation parameters for using a dental prosthesis may comprise determining the size and/or the shape of the respective dental prosthesis.

For example, one or more of the treatment options further comprise preparing the teeth for the dental prostheses. The preparing comprises removing tooth substance to shape a support surface configured for supporting the dental prosthesis.

For example, one or more teeth may have to be prepared in order to provide a suitable support surface configured for supporting a veneer. The preparing of the respective teeth may comprise generating preparation by removing tooth substance in order to shape the required support surface. For this purpose, a surface of a tooth, e.g., a lingual surface, may be shaped to provide a sufficient support surface for a veneer.

For example, the preparing of the teeth may comprise a preparing for a dental prosthesis. In order to provide a support surface suitable for supporting the respective dental prosthesis, e.g., a crown, tooth substance may have to be removed.

For example, the implementation parameters for one or more of the measures of the treatment options comprises determining one or more sections of teeth comprising the tooth substance to be removed.

Determining the implementation parameters may comprise determining one or more section of the teeth to be removed in order to provide a suitable preparation with suitable support surfaces for supporting, e.g., veneers or grounds. Using the current state model, it may be determined, whether a removal of the sections defined by the implementation parameters may result in remaining tooth structures, which are suitable for the treatment option being checked. Thus, the feasibility requirements for the respective treatment option may be checked.

For example, the feasibility requirements comprise one or more of the following requirements: sufficient wall thickness of the dental prostheses used as measures of the treatment option, sufficient support by the teeth or tooth stumps for the dental prostheses used as measures of the treatment option, sufficient dimensions of the teeth or tooth stumps for enabling a preparation for the dental prostheses used as measures of the treatment option, absence of contraindication.

The feasibility requirements may define a necessary minimal wall thickness required for a dental prosthesis used as a measure of a treatment option. The respective wall thickness of the walls of the respective dental prosthesis, may be necessary in order to ensure a sufficient durability of the respective dental prosthesis and/or stability. The feasibility requirements may define a sufficient support by the tooth or a tooth stump for a dental prosthesis configured to be placed at or on the respective tooth or tooth stump. A sufficient support may ensure that the respective dental prosthesis may be stably bonded to the support surface. Thus, a sufficient retention and resistance by the respective tooth or tooth stump to hold the dental prosthesis may be ensured. The feasibility requirements may comprise definitions of sufficient dimensions of the teeth or tooth stumps for the dental prosthesis. After the preparation, the remaining tooth or tooth stump has required to have sufficient dimension in order to provide a sufficient support for the respective dental prosthesis. For example, a wall thickness of the preparation has to be sufficient in order to ensure a long-term integrity of the respective tooth or tooth stump. Finally, the feasibility requirements may comprise requirements regarding the absence of contraindication for the respective treatment option.

For example, the contraindications comprise one or more of the following: bruxism, tooth damage.

A contraindication may for example comprise bruxism. Bruxism refers to excessive teeth grinding or jaw clenching. Bruxism is an oral parafunctional activity, i.e., unrelated to normal oral function like eating or talking. Symptoms commonly associated with bruxism may, e.g., comprise tooth wear and damage to dental restorations.

Bruxism may for example be contraindication for veneers, since by grinding the teeth, veneers may be loosened. Furthermore, a contraindication may comprise tooth damage. Tooth damage may, e.g., comprise caries. In case a tooth is damaged, depending on the extent of the damage, it may be required to remove the respective tooth. Removing a tooth may exclude a usage of a veneer or crown but may require an implant.

For example, additional scan data is provided for checking the feasibility requirements. For example, additional scan data may be acquired for checking the feasibility requirements. Using the additional scan data, e.g., the presence of contraindications may be checked. The additional scan data may, e.g., comprise NIRI data. The additional scan data may, e.g., comprise X-ray data. For example, the additional scan data may comprise tomography data acquired, e.g., using CBCT. Alternatively or additionally, various other types of imaging methods of oral and maxillofacial radiology may be used to acquire the additional scan data. The additional scan data may provide information about the structure of the teeth, in particular about internal structures of the teeth. Using the additional scan data, e.g., bruxism and/or tooth damages, like caries, may be detected.

For example, the treatment options are ordered according to a ranking order. The provided treatment options are checked subsequently following the ranking order, until the dentition is determined to meet the feasibility requirements assigned to the treatment option being checked. In case the dentition is determined to meet the feasibility requirements assigned to the treatment option being checked, the checking is interrupted.

For example upon receiving a continuation command via the user, the checking is continued with the next treatment option following the ranking order upon receiving a continuation command. The continuation command may, e.g., be provided in form of a rejecting command rejecting the treatment proposal. In response to such a rejection, the checking may be continued in order to find an alternative treatment option with feasibility requirements met by the dentition.

For example, in case the dentition is determined to meet the feasibility requirements, the checking may be interrupted. For example, the treatment option meeting the feasibility requirement may be provided in form of a treatment proposal as an output. Thus, a user may decide whether the respective treatment option is an acceptable proposal for a treatment. In that case, the user may for example terminate the checking and use the suggestion provided by the computer system. In case the user is not satisfied with the proposal by the computer system, the computer system may receive a continuation command initiating a continuation of the checking with the next treatment option following the ranking order of the treatment options. The checking may be continued by respective continuation commands until a treatment option is found that satisfies the user or no further treatment options are available. In case no further treatment options are available, the checking may be terminated automatically.

For example, the interruption of the checking may cause a terminating of the checking. When a suitable treatment option is found meeting the feasibility requirements, the checking may thus be terminated.

For example, all of the treatment options of the set of treatment options are checked and a set of feasible treatment options is determined. For each of the feasible treatment options the dentition is meeting the feasibility requirements assigned to the respective feasible treatment option. The treatment proposal comprises the set of feasible treatment options and identifies for each of the feasible treatment options of the set of feasible treatment options implementation parameters determined for the measures of the respective feasible treatment option.

For example, all of the treatment options may be checked. Those treatment options, which meet the feasibility requirements, may be provided as a possible treatment proposal. Thus, a plurality of alternative treatment proposals may be provided as an output. The respective alternative treatment proposals may be provided according to the ranking order. For example, one after another may be provided as an output in order to enable a user to select one of the alternative treatment proposals. For example, all the alternative treatment proposals may be provided as an output with an indication of their ranking order. Thus, the user may be enabled to select one of the alternative treatment proposals.

For example, the providing of the set of treatment options comprises providing as an output via a user interface of the computer system a predefined set of selectable treatment options, in response to the providing, receiving via the user interface as an input the set of treatment options comprising treatment options selected from set of selectable treatment options.

For example, the user may select the set of treatment options from a set of selectable treatment options. Thus, the user may decide which of the treatment options are suitable and thus worth considering. These suitable treatment options may be selected by the user and form the set of treatment options. In addition, the user may be enabled to alter the ranking order of the set of treatment options selected from the set of selectable treatment options. In order to enable the user to select treatment options in order to define the set of treatment options, an output of selectable treatment options may be provided. Thus, the user may be enabled to check the output and select those treatment options which are suitable.

For example, the input furthermore comprises a definition of the ranking order of the selected treatment options. By defining the ranking order, preferences of the users may be provided to the computer system.

For example, digital preparations of one or more teeth, i.e., 3D digital models of preparations, may be defined adjusted for dental prosthesis, like a veneer or crown, to be used as a measure of a treatment option. The preparations may be subtracted from the current state model and/or from the target state model, determining the extent of preparation required to prepare the current dentition for the veneers or crowns.

For the subtraction, e.g., a Boolean subtraction, a deformation and smoothening (iteratively, if necessary) or using boundary curves projecting the current state model, i.e., scan data. In case of using a boundary curve projecting the current state model, a mesh defining the current state model may only be deformed in the vicinity of the boundary curve such that the two meshes of the current state model and the preparation may fit exactly on top of each other in the vicinity of the boundary curve. The current state model may be cut there, i.e., where the meshes fit and replaced with a provisional surface defining a support surface or bottom surface of the veneer or crown.

In another aspect, the invention relates to a computer program product for providing a treatment proposal for a dentition of a patient. The computer program product comprises a computer readable storage medium having program instructions embodied therewith. The program instructions being executable by a processor of a computer system to cause the computer system to provide a 3D digital model of a current state of the dentition as a current state model using scan data of the dentition. Furthermore, a 3D digital model of a target state of the dentition to be achieved as a target state model is provided. The target state model is generated using the current state model. A set of treatment options for treating the dentition is provided. Each of the treatment options define one or more pre-defined measures of dentition modifications. Each of the treatment options are assigned with a set of one or more feasibility requirements to be met by the dentition for the treatment option to be feasible. One or more of the provided treatment options are checked. The checking comprises determining, whether the dentition of the patient is meeting the feasibility requirements assigned to the treatment option being checked using the current state model. In case the dentition is determined to meet the feasibility requirements assigned to the treatment option being checked, the treatment proposal is provided. The treatment proposal identifies the respective treatment option and implementation parameters determined for the measures of the identified treatment option. The implementation parameters are determined for modifying the current state model such that one or more discrepancies of the current state model relative to the target state model are compensated.

The program instructions provided by the computer program product may be configured to be executed by any of the aforementioned examples of a computer system for providing a treatment proposal for a dentition of a patient.

For example, the program instructions may implement a method providing an automatic treatment selection automatically selecting a treatment option for a dental treatment, e.g., reconstruction. The automatically selected treatment option may be provided as a treatment proposal. The treatment options of the set of treatment options may, e.g., be treatment options for improving the aesthetic appearance of a smile of a patient.

In another aspect, the invention relates to a computer-implemented method for providing a treatment proposal for a dentition of a patient. The method comprises providing a 3D digital model of a current state of the dentition as a current state model using scan data of the dentition. Furthermore, a 3D digital model of a target state of the dentition to be achieved as a target state model is provided. The target state model is generated using the current state model. A set of treatment options for treating the dentition is provided. Each of the treatment options define one or more pre-defined measures of dentition modifications. Each of the treatment options are assigned with a set of one or more feasibility requirements to be met by the dentition for the treatment option to be feasible. One or more of the provided treatment options are checked. The checking comprises determining, whether the dentition of the patient is meeting the feasibility requirements assigned to the treatment option being checked using the current state model. In case the dentition is determined to meet the feasibility requirements assigned to the treatment option being checked, the treatment proposal is provided. The treatment proposal identifies the respective treatment option and implementation parameters determined for the measures of the identified treatment option. The implementation parameters are determined for modifying the current state model such that one or more discrepancies of the current state model relative to the target state model are compensated.

The computer-implemented method may be configured to be executed by any of the aforementioned examples of a computer system for providing a treatment proposal for a dentition of a patient.

For example, the computer-implemented method may provide an automatic treatment selection automatically selecting a treatment option for a dental treatment, e.g., reconstruction. The automatically selected treatment option may be provided as a treatment proposal. The treatment options of the set of treatment options may, e.g., be treatment options for improving the aesthetic appearance of a smile of a patient.

The aforementioned method executed using an apparatus comprising a computer. For example, the method may be executed is by a computer system for providing a treatment proposal for a dentition of a patient. The computer system may comprise a processor and a memory storing program instructions executable by the processor. Execution of the program instructions by the processor may causes the computer system to execute the aforementioned method.

The above-described examples and embodiments may be combined freely as long as the combinations are not mutually exclusive.

BRIEF DESCRIPTIONS OF THE DRAWINGS

In the following, embodiments of the invention are described in greater detail in which FIG. 1 shows a flowchart illustrating an exemplary method for providing a treatment proposal;

In the following similar features are denoted by the same reference numerals.

DETAILED DESCRIPTION

Figure 1:
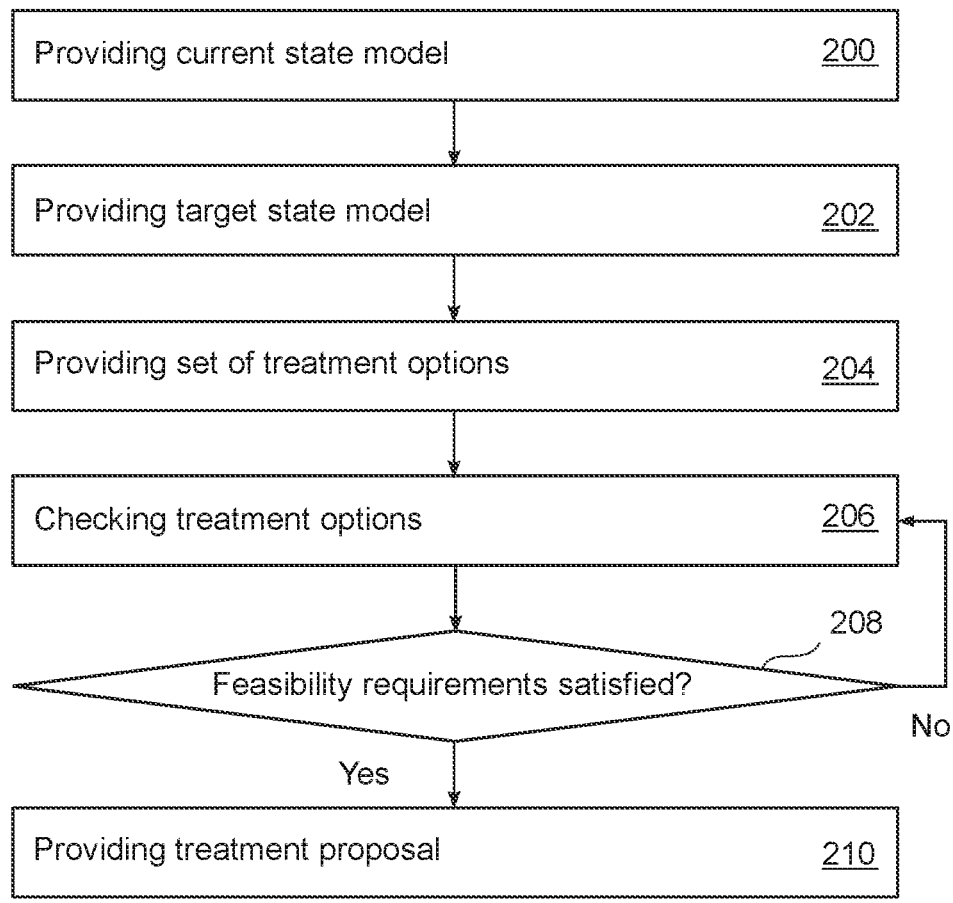

FIG. 1 shows an exemplary computer-implemented method for providing a treatment proposal for a dentition of a patient. In block 200, a 3D digital model of a current state of the dentition is provided as a current state model. For providing the current state model, scan data of the dentition may be used. This scan data may be acquired using an intraoral optical scan of the surface of the teeth and the gingiva of the patient. For example, an impression of the dentition or a physical model, like a plaster cast, may be scanned using an optical scanner to acquire the scan data. The scan data may further comprise NIRI data. The scan data may further comprise X-ray data. For example, the scan data may further comprise tomography data acquired, e.g., using CBCT. Alternatively or additionally, various other types of scan data may be acquired using imaging methods of oral and maxillofacial radiology.

In block 202, a 3D digital model of a target state of the dentition to be achieved is provided as a target state model. The target state model is generated using the current state model. For example, the individual teeth of the current state model may be modified regarding their position, orientation, size and/or shape. For example, individual teeth of the current state model may be replaced with 3D digital models of teeth from a tooth library. The respective library teeth may be adjusted rearing position and/or orientation to the state defined by the current state model. Furthermore, size and/or shape of the library teeth may be modified.

In block 204, a set of treatment options for treating the dentition is provided. The treatment option may, e.g., comprise using veneers, using crowns, using prostheses, like crowns and bridges anchored using implants, and/or orthodontic measures. The treatment options may, e.g., be ordered according to a ranking order. For example, the ranking order may be based on the extend of preparation required for the respective treatment options. A veneer may require non or only minimal preparation. Using a crown may require a preparation of a tooth stump, i.e., significant removal of healthy tooth tissue. Using an implant may require to completely remove a tooth. Furthermore, the ranking may take into account the achievable effects. For example, orthodontic measures may be defined as a fallback treatment option, if the other treatment options are not feasible. Furthermore, other ranking criteria may be taken into account. Even individual preferences of the patient and/or the costs of the different treatment options may be taken into account.

Each of the treatment options defines one or more predefined measures of dentition modifications, e.g., using veneers, crowns, implants in combination with crowns or bridges, or braces. Each of the treatment options is assigned with a set of one or more feasibility requirements to be met by the dentition for the treatment option to be feasible. For example, the teeth have to be suited for a suitable preparation for the respective treatment option. For example, the teeth may have to provide a suitable support surface. For example, the teeth may have to provide a sufficient support for the respective treatment option. For example, the current state may have to provide sufficient space for implementing the respective treatment option. Providing sufficient space may be required for designing, e.g., veneers or crowns, with a sufficient thickness. Furthermore, an absence of contraindications may be required. A contraindication for veneers may, e.g., be bruxism and/or tooth damage, like caries. A contraindication for crowns without an implant may, e.g., be extensive tooth damage.

For determining the presence of possible contraindications additional scan data, like NIRI data, panoramic radiographic data and/or CBCT data. NIRI data, panoramic radiographic data and/or CBCT data may, e.g., be used to determine the inner structure of a tooth. For example, it may be determined how much tooth tissue, like enamel and dentin, is present around the pulp of the tooth. Depending on this determination, it may be assessed, how much tooth tissue can be removed without endangering the pulp and thus the life of the tooth. For example, scan data may be used to determine current filling of the teeth. These fillings may be digitally removed from the current state model, in order to determine how much natural tooth tissue remains for a preparation. For example, it may be assessed, whether sufficient residual tooth tissue is available to prepare a sufficient support for a crown. If there is not sufficient residual tooth tissue available, the tooth may have to be removed completely and, e.g., an implant may have to be used to support the crown. Furthermore, bruxism may be determined using the scan data. Bruxism may, e.g., be determined based on the wear of the teeth. In case of bruxism, e.g., no usage of veneers may be possible due to the risk of a chipping of the veneers.

In block 206, one or more of the provided treatment options are checked, e.g., subsequently following the ranking order. The checking for a given treatment option comprises determining, whether the dentition of the patient is meeting the feasibility requirements assigned to the treatment option being checked using the current state model. In block 208, it is decided based on the result of the checking, how the method continues. In case the dentition is determined to meet the feasibility requirements assigned to the treatment option being checked, the method continues with block 210.

In block 210, a treatment proposal is provided identifying the respective treatment option, for which the feasibility check in block 208 was positive, as well as implementation parameters determined for the measures of the identified treatment option. The implementation parameters are determined for the measures of the identified treatment option to modify the current state model such that one or more discrepancies of the current state model relative to the target state model are compensated. For example, the implementation parameters are determined such that the current state model applying the implementation parameters is modified such that it matches the target state model. For the determining in block 206, e.g., the implementation parameters may be determined and taken into account.

In case the feasibility check in block 208 is negative, the method may continue with checking the next treatment option according to the ranking order. This may be continued, until a treatment option is found satisfying the feasibility requirements. In case no treatment options are left, the method may terminate with an error message. For example, the method may be terminated, when block 210 is reached. For example, the method may be continued with block 206, in case a rejection command rejecting the treatment proposal is received, e.g., via an input device of the computer system used for executing the method. For example, the method may be terminated with block 210, in case an acceptance command accepting the treatment proposal is received, e.g., via an input device of the computer system used for executing the method.

Figure 2:
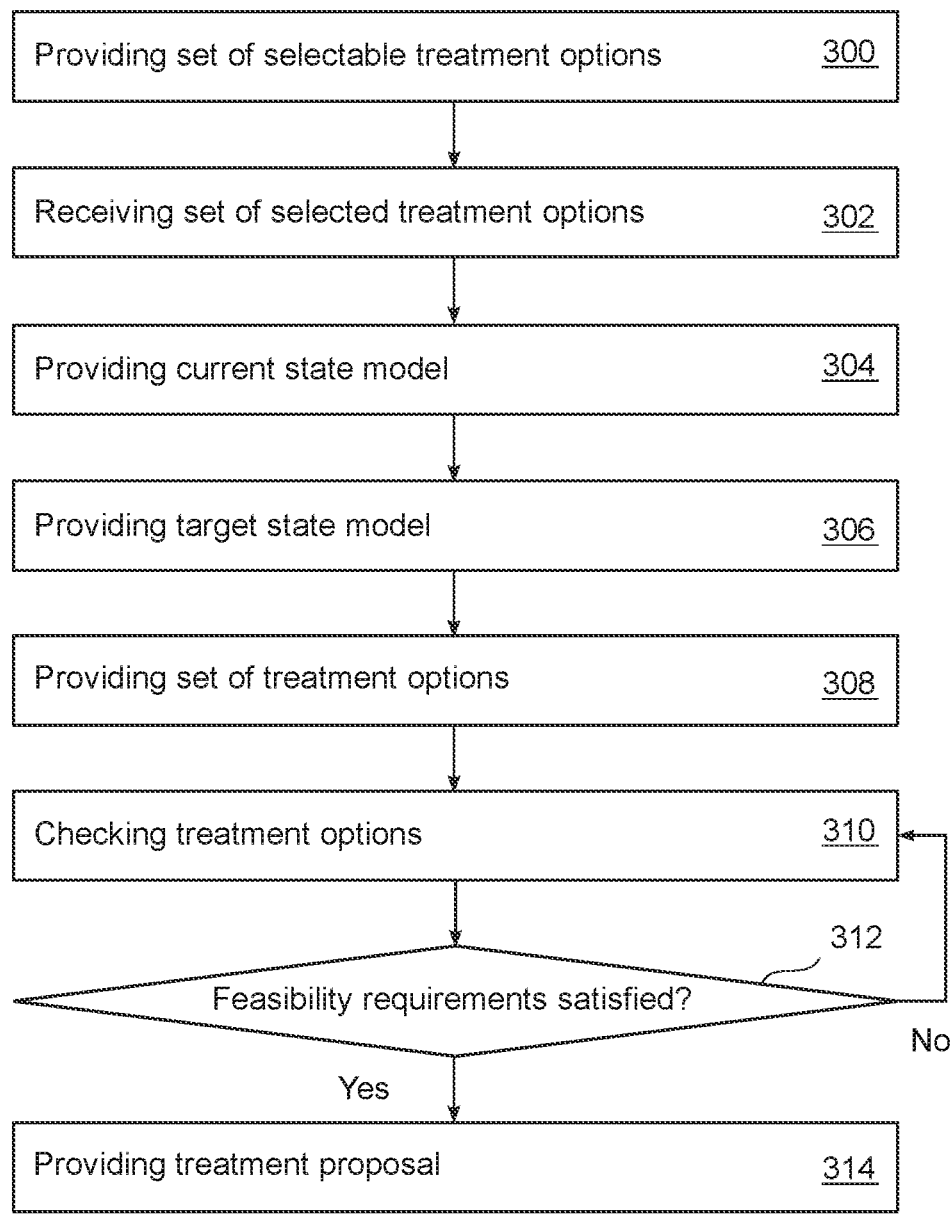
FIG. 2 shows a flowchart illustrating an exemplary method for providing a treatment proposal.

FIG. 2 shows a further exemplary computer-implemented method for providing a treatment proposal for a dentition of a patient. Blocks 304 to 314 of FIG. 2 are identical to blocks 200 to 210 of FIG. 1. In addition to blocks 304 to 314, FIG. 2 comprises in block 300 providing a predefined set of selectable treatment options, e.g., using an output device of the computer system used for executing the method. For example, the predefined set of selectable treatment options may be provided on a graphical user interface displayed on a display of the computer system. A user may thus be enabled to select the treatment options to be comprised by the set of treatment options provided in block 308. In response to the output of the predefined set of selectable treatment options, an input may be received in block 302 with the set of treatment options comprising treatment options selected from set of selectable treatment options. The input may, e.g., be via an input device of the computer system used for executing the method. For example, the input may furthermore comprise a definition of the ranking order of the selected treatment options. For example, the output in block 300 may comprise a proposed ranking order, which may be accepted or altered by the input received in block 302.

Figure 3:
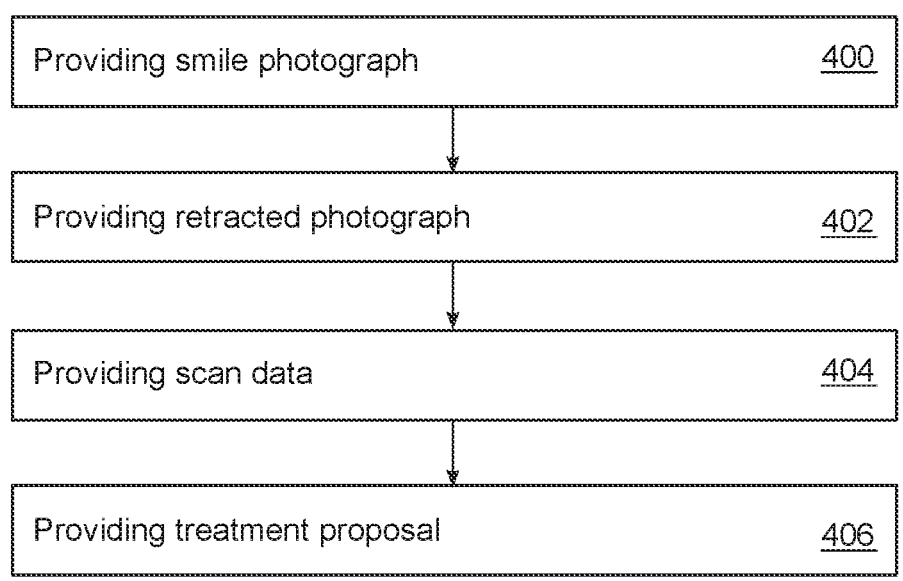
FIG. 3 shows a flowchart illustrating an exemplary method for providing a treatment proposal.

FIG. 3 shows a further exemplary computer-implemented method for providing a treatment proposal for a dentition of a patient. The method of FIG. 3 may, e.g., be used for providing a treatment proposal for improving the aesthetic appearance of a smile of the patient. In block 400, a smile photograph of a patient may be provided, e.g., be taken using a digital camera. The smile photograph may show a smile of the patient, i.e., depicting the smiling patient. In block 402, a retracted photograph may be provided, e.g., be taken using a digital camera. In the retracted photograph, the patient's lips may be retracted or pushed back with the help of a plastic mouthpiece, e.g., a transparent mouthpiece, to reveal the teeth of the patient as much as possible. The smile photograph and the retracted photograph may both be 2D photographs. In block 404, the 3D scan data required for generating the 3D current state model and/or for checking the feasibility requirements may be provided, e.g., be acquired using a suitable scanner. In block 406, a treatment proposal may be provided. Providing the treatment proposal may comprise executing the method of FIG. 1, i.e., blocks 200 to 210, or executing the method of FIG. 2, i.e., blocks 300 to 314.

The photographs provided in blocks 400 and 402 may be registered with the 3D current state model provided using the scan data of block 404. The registration may for example use a point registration or an automatic registration using machine learning may be implemented. For example, the retracted photograph of block 402 depicting more of the patient's teeth than the smile photograph of block 400 may be used to register the 3D current state model of the dentition with the 2D teeth of the photographs of the teeth. The retracted photograph of block 402 and the smile photograph of block 400 may be registered with each other, e.g., using the parts of the teeth shown on both photographs. The smile photograph of block 400 may be placed lingual in front of the current state model with the smile being cut out along the lip lines such that in the mouth of the patient the teeth of the 3D model may be visible instead of the teeth depicted in the smile photograph. For placing the smile photograph of block 400 the registration of the smile photograph with the retracted photograph of block 402 may be used. Alternatively, only the smile photograph may be used and registered with the current state model before cutting out the teeth, in case the teeth sections shown in the smile photograph are sufficient for a registration.

This placement of the smile photograph of block 400 in front of the current state model may allow to see the current state model through the cut-out of the smile photograph. The current state model may be modified, providing the target state model. By replacing the current state with the target state model, the effect of the modifications may be visualized in context of the 2D smile photograph. Thus, a realistic impression of the aesthetic appears of possible 3D modifications of the patient dentition may be provided in the 2D photograph. In particular, the effects of such modifications on the aesthetic appearance of the patient's smile may be illustrated.

After generating a satisfying target state model and, e.g., checking the aesthetic effect of the respective target state model on the smile of the patient, a treatment proposal for the dentition of the patient in order to achieve the target model may be provided in block 406.

Figure 4:
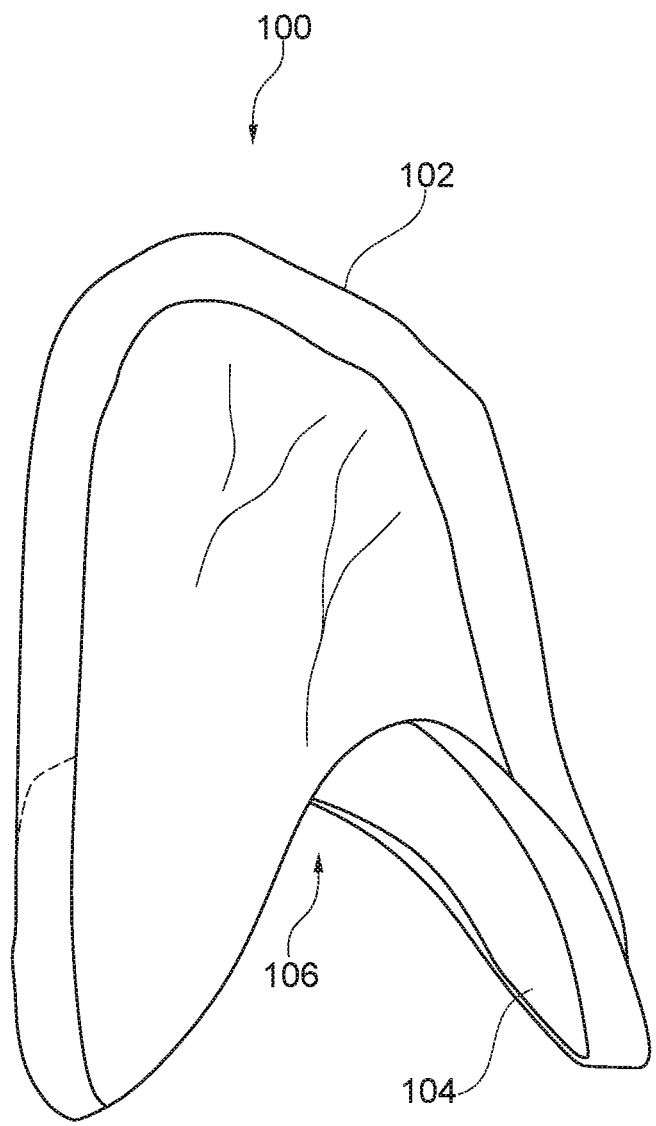
FIG. 4 shows an exemplary 3D digital model of a crown.

FIG. 4 shows an exemplary 3D digital model of a crown 100. For example, the crown 100 may be generated. This crown 100 may be generated in minimal form, i.e., such that the preparation of the natural tooth in order to apply the crown is kept minimal. The crown 100 may be generated to match the outer form of a library tooth of a target state model. For example, the library tooth may define the margin within which the crown 100 the crown may be generated. The library tooth may for example be adapted to a bonding curve and/or bonding surface 104 of the respective crown 100. It may be checked, whether the feasibility requirements for the crown 100 are met.

For the crown 100, the feasibility requirements may require that a prepared tooth stump, on which the crown 100 is to be placed, does not become too thin and/or pointed. To ensure that the tooth stump does not become too thin and/or pointed, the clearance 106 defined by the bonding surface 104 may be required to have a sufficient size, e.g., width and/or height. The respective tooth stump may, e.g., be represented by the adapted library tooth. In order to check the respective feasibility requirement, a ball with a diameter resembling a required diameter of the tooth stump, e.g., an intended maximum diameter or a required minimum diameter, may be placed within a clearance 106 of the 3D digital model of the crown 100. The clearance 106 is intended for receiving the respective tooth stump. It may be checked that the ball does not or only within pre-defined limits penetrate the bonding surface 104 of the 3D digital model of the crown 100 defining the clearance 106. In case the ball resembling the required minimum diameter does not or only within pre-defined limits penetrate the bonding surface 104, the clearance 106 limited by the bonding surface 104 provides sufficient space for a prepared tooth stump with a suitable minimum size. Thus, it can be ensured that the tooth stump does not have to be reduced to a degree that it becomes, e.g., too thin and/or pointed.

Furthermore, the feasibility requirements may require a thickness of the crown 100, i.e., a material thickness, to be equal or larger than a predefined minimum thickness. The predefined minimum thickness may ensure that the crown 100 comprises a sufficient material thickness and thus stability, especially around the tooth stump on which the crown 100 is arranged. In general, it may be a goal to conserve as much of a remaining tooth stump as possible, i.e., to minimize the required amount of tooth material to be removed. Therefore, e.g., a required diameter of the tooth stump be defined and indicated by a ball as described above. This required diameter may e.g., be an intended maximum diameter for which only a minimal amount of tooth material is removed or a required minimum diameter ensuring that the tooth stump does not become too thin and/or pointed. For this required diameter of the tooth stump, it may be checked whether a crown, like crown 100, can be provided meeting the minimum thickness requirement. In case the minimum thickness requirement cannot be met for a given diameter of the tooth stump, it may, e.g., be checked, whether the minimum thickness requirement can be met with a reduced diameter of the tooth stump.

In order to check the minimum thickness of the crown 100, a distance between the outer surface 102 of the crown 100 opposing a bonding surface 104 of the crown 100, i.e., an inner surface of the crown, may be measured. It may be checked. Whether the measured distance is larger than the required minimum thickness. For example, it may be determined in which sections of the crown 100, e.g., laterally, the distance becomes minimal. For this minimal distance, it may, e.g., be checked, whether the distance exceeds the required minimum thickness. In case the minimum thickness requirement is locally violated, the crown 100 may, e.g., be regenerated with a larger thickness. For example, the size of the clearance 106 may be reduced, in order to increase the material thickness of the crown 100. In this case, it may, e.g., have to be re-checked, whether it is still possible to prepare a tooth stump with a sufficiently large diameter. It may be checked, whether for a crown 100 generated within the margin defined by the library tooth and comprising a larger thickness, e.g., due to a reduction of the clearance 106, the reduced clearance 106 is still large enough to allow for a suitably prepared tooth stump, which, e.g., is neither to too thin nor pointed. In case such a reduced clearance 106 is too small for a suitably prepared tooth stump, the treatment option of using a crown may be rejected.

According to the example above, the design of the crown 100, i.e., the geometrical form of the outer surface 102, may be defined may the 3D digital model of the target state. Alternatively, design changes of the crown 100 may be allowed, i.e., deviations from the form defined by the target state. For example, such deviations may only be allowed within a predefined range and/or within predefined sections of crown 100. In case the minimum thickness requirement cannot be met with the design defined by the target state, it may be checked, whether minimum thickness requirement can be with design changes, within the predefined range and/or within predefined sections of crown 100. For example, by moving the outer surface 102, e.g., laterally outwards, the lateral thickness of the crown 100 may be increased. This may, e.g., be achieved by locally increasing a convex curvature of the crown 100. For example, the design changes may be restricted to a lingual or palatial section of the crown 100. For example, the design may be extended lingually or palatinally, i.e., the thickness of the crown may be increased lingually or palatinally. Such a lingual or palatial deviation may, e.g., neither affect the aesthetics, i.e., the visible aesthetics, nor the function of the crown 100. The predefined range of allowable changes may be area dependent. In some sections or areas of the crown 100, like a lingual or palatial section, larger changes may be tolerable, while in other sections only slight changes of the design may be tolerable. Thus, the feasibility of the crown 100 may be achievable by a minimal change of the design. For example, such design changes may be checked, in case the minimum thickness requirement cannot be met. In case it is determined that the minimum thickness requirement can be met with a design change within predefined limits, e.g., within a predefined range and/or within a predefined sections of crown 100, the design change may be suggested.

The amended design suggestion may be provided in case the original design was not feasible, while the amended design is feasible. For example, the user may be able to decide whether to accept the suggested design amendment as a treatment option to be further checked. In case an instruction to accept the amended design suggestion as a treatment option, it may be further checked. In case this treatment option meets all the feasibility requirements assigned to the respective treatment option, a treatment proposal may be provided identifying the respective treatment option. The design change may, e.g., be provided as a part of the implementation parameters, in case the treatment option comprising the crown 100 is determined to meet the feasibility requirements assigned to respective treatment option.

Alternatively, the 3D digital model of a crown 100 may be provided with a material thickness, which is for the whole crown 100, in particular laterally, equal or larger than the required minimum thickness. It may than be checked for such a crown 100, as a feasibility requirement that a prepared tooth stump, on which the crown 100 is to be placed, does not become too thin and/or pointed. This check may be performed as described above, e.g., using a ball indicating a suitable size of the tooth stump. In case the clearance 106 of such a crown 100 is too small for a suitably prepared tooth stump, the treatment option of using a crown may be rejected.

Alternatively or additionally, further parameter for crown 100 may be checked, like height, angulation and/or distance to other teeth. For theses parameters it may be checked, whether suitable values can be implemented, while meeting the minimum thickness requirement.

In a similar way, a 3D digital model of a veneer may be provided. For providing a veneer the crown 100 shown in FIG. 4 may be cut in half a long a vertical cutting line.

Figure 5:
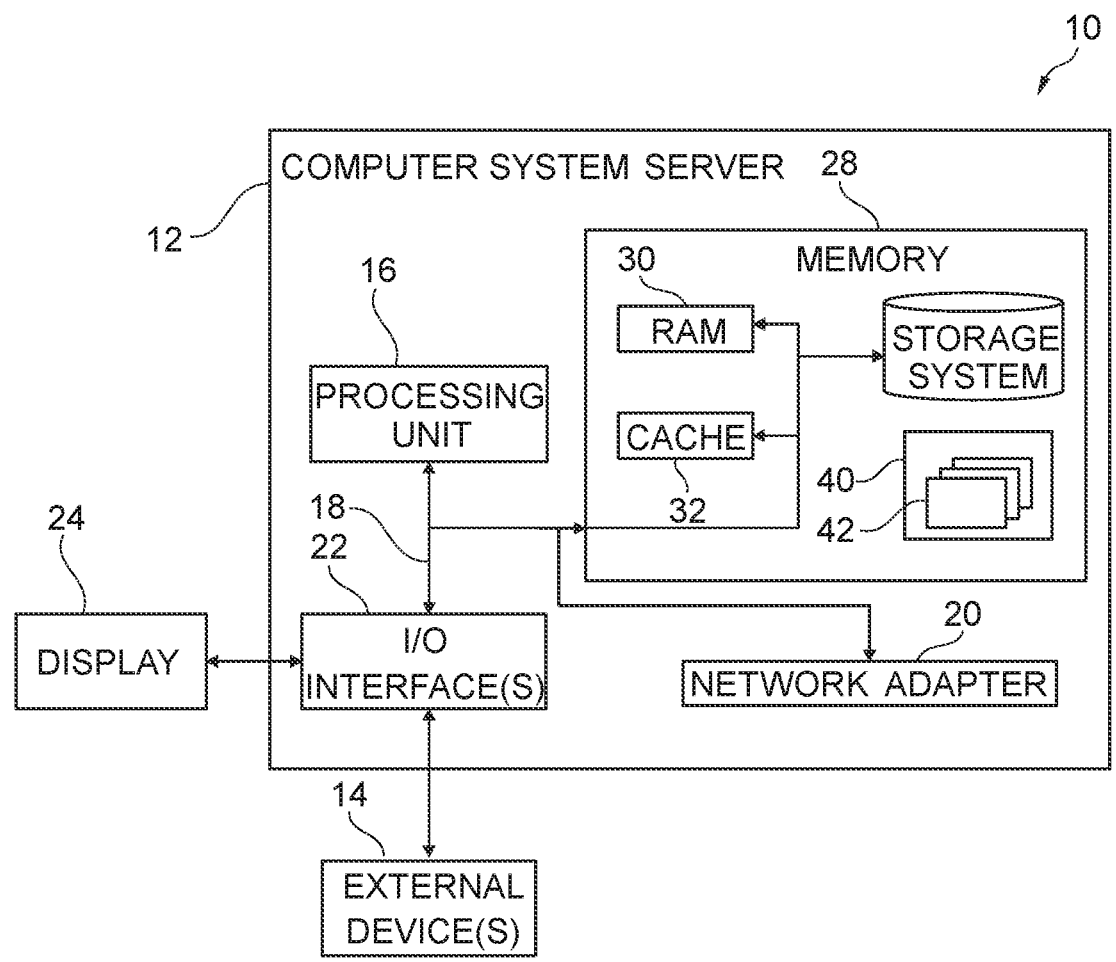
FIG. 5 shows an exemplary computer system for providing a treatment proposal.

FIG. 5 shows a schematic diagram of an exemplary computer system 10 for providing a treatment proposal for a dentition of a patient. The computer system 10 may be operational with numerous other general-purpose or special-purpose computing system environments or configurations. Computer system 10 may be described in the general context of computer system executable instructions, such as program modules comprising executable program instructions, being executable by the computer system 10. Generally, program modules may include routines, programs, objects, components, logic, data structures, and so on that perform particular tasks or implement particular abstract data types. Computer system 10 may be practiced in distributed computing environments where tasks are performed by remote processing devices that are linked through a communications network. In a distributed computing environment, program modules may be located in both local and remote computer system storage media including memory storage devices.

In FIG. 5, computer system 10 is shown in the form of a general-purpose computing device. The components of computer system 10 may include, but are not limited to, one or more processors or processing units 16, a system memory 28, and a bus 18 that couples various system components including system memory 28 to processor 16. Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system 10 may comprise a variety of computer system readable storage media. Such media may be any available storage media accessible by computer system 10, and include both volatile and non-volatile storage media, removable and non-removable storage media.

A system memory 28 may include computer system readable storage media in the form of volatile memory, such as random-access memory (RAM) 30 and/or cache memory 32. Computer system 10 may further include other removable/non-removable, volatile/non-volatile computer system storage media. For example, storage system 34 may be provided for reading from and writing to a non-removable, non-volatile magnetic media also referred to as a hard drive. For example, a magnetic disk drive for reading from and writing to a removable, non-volatile magnetic disk, e.g., a floppy disk, and an optical disk drive for reading from or writing to a removable, non-volatile optical disk such as a CD-ROM, DVD-ROM or other optical storage media may be provided. In such instances, each storage medium may be connected to bus 18 by one or more data media interfaces. Memory 28 may include at least one program product having a set of program modules, e.g., at least one program module, configured to provide a treatment proposal for a dentition of a patient.

Program 40 may have a set of one or more program modules 42 and by way of example be stored in memory 28. The program modules 42 may comprise an operating system, one or more application programs, other program modules, and/or program data. Each of the operating system, one or more application programs, other program modules, and program data or some combination thereof, may include an implementation of a networking environment. One or more of the program modules 42 may provide a treatment proposal for a dentition of a patient.

Computer system 10 may further communicate with one or more external devices 14 such as a keyboard, a pointing device, like a mouse, and a display 24 enabling a user to interact with computer system 10. Such communication can occur via input/output (1/O) interfaces 22. Computer system 10 may further communicate with one or more networks such as a local area network (LAN), a general wide area network (WAN), and/or a public network, like the Internet, via network adapter 20. Network adapter 20 may communicate with other components of computer system 10 via bus 18. It should be understood that although not shown, other hardware and/or software components could be used in conjunction with computer system 10.

The computer system 10 shown in FIG. 5 may be configured for providing a treatment proposal for a dentition of a patient. The computer system 10 may be a standalone computer with no network connectivity that may receive data to be processed through a local interface. The data received by computer system 10 may for example comprise scan data of a patient's mouth from an intraoral scan or from a scan of a classical mold/impression, e.g., providing information about the surface structure of the patient's tissue on which the denture is to be placed. This data may be used to generate the digital 3D digital model of the denture. Alternatively, the data received may, e.g., comprise digital 3D digital model of the denture. The computer system 10 may be used to provide a treatment proposal for a dentition of a patient. Such operation may, however, likewise be performed using a computer system that is connected to a network such as a communications network and/or a computing network.

Figure 6:
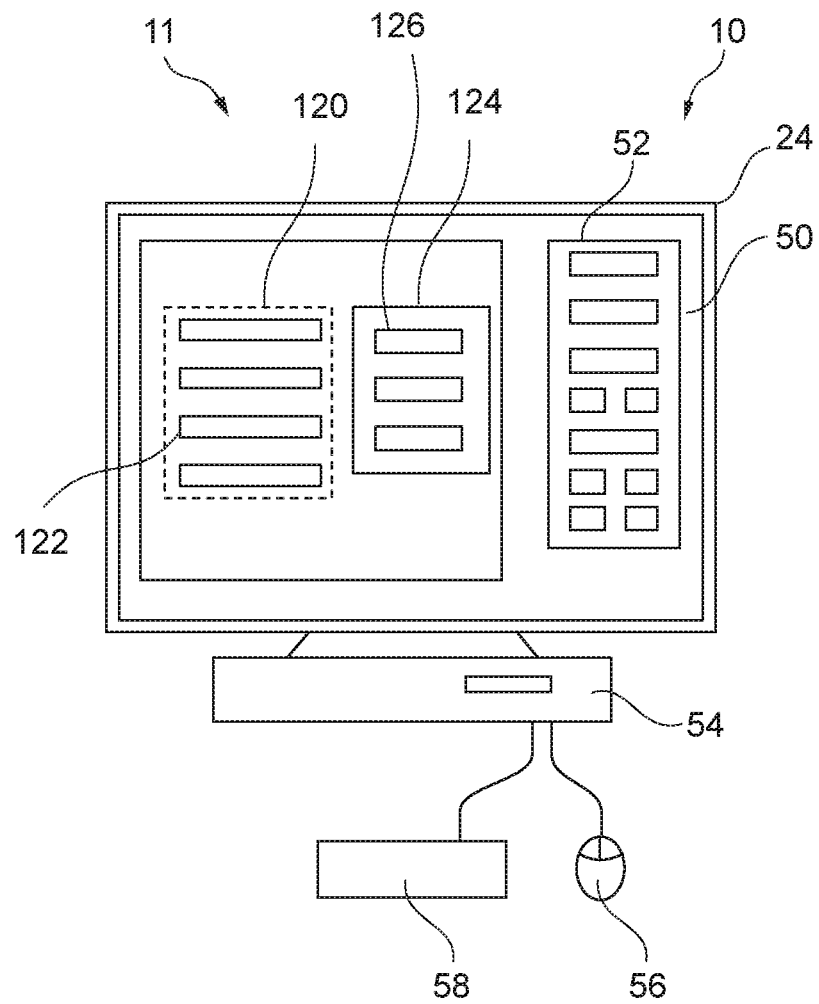
FIG. 6 shows an exemplary system for providing a treatment proposal.

FIG. 6 shows an exemplary system 11 comprising a computer system 10 for providing a treatment proposal 124 for a dentition of a patient. The computer system 10 may for example be configured as shown in FIG. 5. The computer system 10 may comprise a hardware component 54 comprising one or more processors as well as a memory storing machine-executable program instructions. Execution of the program instructions by the one or more processors may cause the one or more processors to control the computer system 10 to provide a set 120 of treatment options 122 for treating the dentition. The treatment options 122 may, e.g., be ordered according to a ranking order. Execution of the program instructions may further cause the one or more processors to control the computer system 10 to check one or more of the provided treatment options 122, e.g., subsequently following the ranking order, whether the dentition is meeting feasibility requirements assigned to the respective treatment option 122. In case the dentition is determined to meet the feasibility requirements assigned to the treatment option 122 being checked, the treatment proposal 124 is provided. The treatment proposal 124 may identify the respective treatment option as well as implementation parameters determined for the identified treatment option. The implementation parameters may be provided in form of treatment instructions 126, instruction a user on how to implement the treatment option according to the treatment proposal 124.

The computer system 10 may further comprise one or more input devices, like a keyboard 54 and a mouse 56, enabling a user to interact with the computer system 10. Furthermore, the computer system 10 may comprise one or more output devices, like a display 24 providing a graphical user interface 50 with control elements 52, e.g., GUI elements, enabling the user to control the providing of the treatment proposal 124 using the computer system 10. Furthermore, the control elements 52 may, e.g., be used to select treatment options 122 to be comprised by the set 120 of treatment options 122. In addition, the ranking order according to which the treatment options 122 of set 120 of treatment options 122 are ordered may be defined or adjusted using control elements 52. Finally, the control elements 52 may, e.g., be used to accept or reject a treatment proposal 124.

Figure 7:
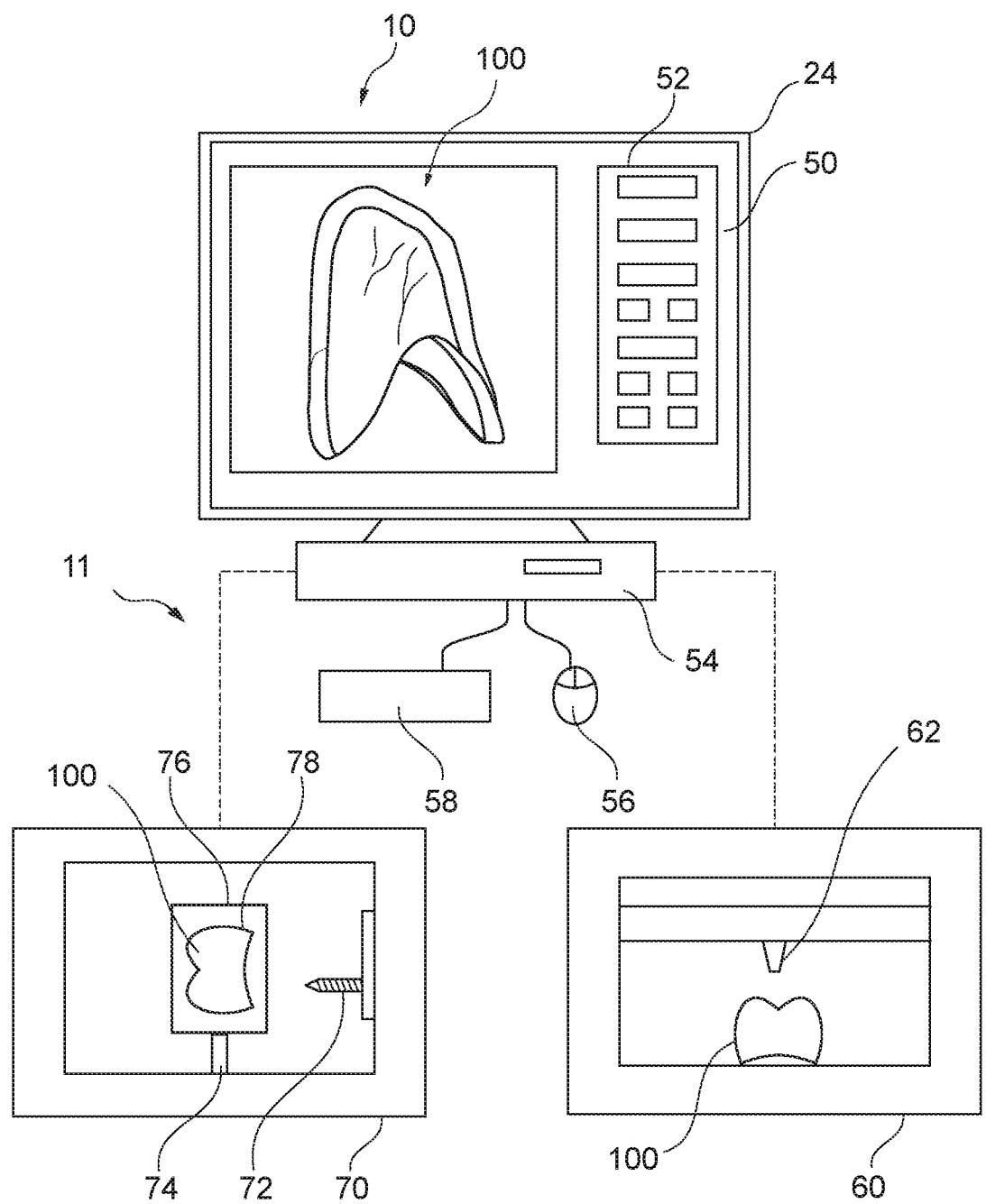
FIG. 7 shows an exemplary system for providing a treatment proposal.

FIG. 7 shows an exemplary system 11 for providing a treatment proposal for a dentition of a patient, which is furthermore configured to manufacture one or more dental element being measures used by a treatment option proposed by the treatment proposal. For example, the treatment option according to the treatment proposal may comprise using one or more crowns 100 defined by 3D digital models. The manufactured model may be a physical copy of the 3D digital model which is used as a template for the manufacturing of the dental element, like the crown 100. The system 11 may comprise the computer system 10 of FIG. 6. The computer system 10 may further be configured to control one or more manufacturing devices 60, 70. For example, the system 11 may comprise a manufacturing device in form of a machining device 70 controlled the computer system 10. The machining device 70 may be configured to machining a blank 76 using one or more machining tools 72. The blank 76 of raw material 78 may be provided using a holding device 74 and cut into a desired final shape and size of the dental element to be manufactured, e.g., the crown 100, using the one or more machining tools 72 for executing a controlled material-removal process. The machining tool 72 may for example be a milling tool. The 3D digital model may provide a template of the dental element manufactured using the machining device 70.

For example, the system 11 may comprise a manufacturing device in form of a 3D printing device 60. The 3D printing device 60 may be controlled by the computer system 10 and configured to print the dental element to be manufactured, e.g., the crown 100. The 3D printing device 60 may comprise a printing element 62 configured to print the respective dental element, like the crown 100, layer by layer. The 3D digital model may provide a template of the physical dental element manufactured using the 3D printing device 60.

Furthermore, the system 11 may comprise one or more scanner for acquiring scan data to generate a current state model and/or to check feasibility requirements. These scanners may, e.g., comprise an optical scanner configured for performing an intraoral optical scan of the surface of the teeth and the gingiva of the patient. For example, an impression of the dentition or a physical model, like a plaster cast, may be scanned using the optical scanner. The scanners may further comprise an NIRI scanner, an X-ray scanner, and/or a tomography scanner, like a CBCT scanner. The NIRI scanner may, e.g., be integrated into the optical scanner. Alternatively or additionally, various other types of scanners of oral and maxillofacial radiology may be used.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

A single processor or other unit may fulfill the functions of several items recited in the claims. A computer program may be stored/distributed on a suitable medium, such as an optical storage medium or a solid-state medium supplied together with or as part of other hardware, but may also be distributed in other forms, such as via the Internet or other wired or wireless telecommunication systems.

As will be appreciated by one skilled in the art, aspects of the present invention may be embodied as an apparatus, method, computer program or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon. A computer program comprises the computer executable code or "program instructions".

Any combination of one or more computer readable medium(s) may be utilized. The computer readable medium may be a computer readable signal medium or a computer readable storage medium. A "computer-readable storage medium" as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. A further example of an optical disk may be a Blu-ray disk. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

"Computer memory" or "memory" is an example of a computer-readable storage medium. Computer memory is any memory which is directly accessible to a processor. "Computer storage" or "storage" is a further example of a computer-readable storage medium. Computer storage is any non-volatile computer-readable storage medium. In some embodiments, computer storage may also be computer memory or vice versa.

A "processor" as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++, C# or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Generally, the program instructions can be executed on one processor or on several processors. In the case of multiple processors, they can be distributed over several different entities like clients, servers etc. Each processor could execute a portion of the instructions intended for that entity. Thus, when referring to a system or process involving multiple entities, the computer program or program instructions are understood to be adapted to be executed by a processor associated or related to the respective entity.

A "user interface" as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, one or more switches, one or more buttons, and accelerometer are all examples of user interface components which enable the receiving of information or data from an operator.

A GUI element is a data object some of which's attributes specify the shape, layout and/or behavior of an area displayed on a graphical user interface, e.g., a screen. A GUI element can be a standard GUI element such as a button, a text box, a tab, an icon, a text field, a pane, a check-box item or item group or the like. A GUI element can likewise be an image, an alphanumeric character or any combination thereof. At least some of the properties of the displayed GUI elements depend on the data value aggregated on the group of data object said GUI element represents.

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special-purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer-implemented process such that the instructions which execute on the computer or other programmable apparatus provide processes for implementing the functions/acts specified in the flowchart and/or block diagram block or blocks.

Possible advantageous embodiments may comprise the following combinations of features:

1. A computer system for providing a treatment proposal for a dentition of a patient, the computer system comprising a processor and a memory storing program instructions executable by the processor, wherein execution of the program instructions by the processor causes the computer system to:
   provide a 3D digital model of a current state of the dentition as a current state model using scan data of the dentition;
   provide a 3D digital model of a target state of the dentition to be achieved as a target state model, the target state model being generated using the current state model;
   provide a set of treatment options for treating the dentition,
      each of the treatment options defining one or more pre-defined measures of dentition modifications,
      each of the treatment options being assigned with a set of one or more feasibility requirements to be met by the dentition for the treatment option to be feasible;
   check one or more of the provided treatment options, wherein the checking comprises
      determining whether the dentition of the patient is meeting the feasibility requirements assigned to the treatment option being checked using the current state model;
   in case the dentition is determined to meet the feasibility requirements assigned to the treatment option being checked, provide the treatment proposal identifying the respective treatment option and implementation parameters determined for the measures of the identified treatment option for modifying the current state model such that one or more discrepancies of the current state model relative to the target state model are compensated.
2. The computer system of item 1, wherein one or more of the feasibility requirements depend on the implementation parameters of the measures of the treatment option, wherein the determining whether the dentition of the patient is meeting the feasibility requirements assigned to the treatment option being checked is further based on the implementation parameters determined for the treatment option being checked.
3. The computer system of any of the previous items, the providing of the current state model comprising generating the current state model using the scan data.
4. The computer system of item 3, the providing of the current state model comprising acquiring the scan data.
5. The computer system of any of the previous items, the providing of the target state model comprising generating the target state model using the current state model.
6. The computer system of item 5, the generating of the target state model comprising replacing one or more 3D digital models of actual teeth or tooth stumps comprised by the current state model with one or more 3D digital models of teeth from a tooth library.
7. The computer system of any of items 5 to 6, the generating of the target state model comprising modifying one or more features of the following features of one or more 3D digital models of actual teeth or tooth stumps comprised by the current state model: shape, size, orientation.
8. The computer system of any of the previous items, the set of treatment options comprising one or more of the following treatment options using dental prostheses:
using one or more veneers to be arranged on one or more teeth of the dentition as measures of dentition modifications;
using one or more crowns to be arranged on one or more teeth or tooth stumps of the dentition as measures of dentition modifications, the crowns;
replacing one or more teeth or tooth stumps of the dentition as measures of dentition modification,
wherein the replacing comprises extracting one or more teeth from the dentition and inserting one or more dental implants configured for supporting a crown or a bridge.
9. The computer system of item 8, the implementation parameters for one or more of the measures of the treatment options comprising determining on or more of the following: the size of the dental prostheses to be used, the shape of the dental prostheses to be used.
10. The computer system of any of items 8 to 9, one or more of the treatment options further comprising preparing the teeth for the dental prostheses, wherein the preparing comprises removing tooth substance to shape a support surface configured for supporting the dental prosthesis.
11. The computer system of item 10, the implementation parameters for one or more of the measures of the treatment options comprising determining one or more sections of teeth comprising the tooth substance to be removed.
12. The computer system of any of the previous items, the feasibility requirements comprising one or more of the following requirements: sufficient wall thickness of the dental prostheses used as measures of the treatment option, sufficient support by the teeth or tooth stumps for the dental prostheses used as measures of the treatment option, sufficient dimensions of the teeth or tooth stumps for enabling a preparation for the dental prostheses used as measures of the treatment option, absence of contraindication.
13. The computer system of item 12, the contraindications comprising one or more of the following: bruxism, tooth damage.
14. The computer system of any of items 12 and 13, additional scan data being provided for checking the feasibility requirements.
15. The computer system of any of the previous items, the treatment options being ordered according to a ranking order, the provided treatment options being checked subsequently following the ranking order, until the dentition is determined to meet the feasibility requirements assigned to the treatment option being checked, in case the dentition is determined to meet the feasibility requirements assigned to the treatment option being checked, the checking being interrupted.
16. The computer system of item 15, wherein, upon receiving a continuation command via the user interface, the checking is continued with the next treatment option following the ranking order.
17. The computer system of item 15, the interruption of the checking causing a terminating of the checking.
18. The computer system of any of the previous items, wherein all of the treatment options of the set of treatment options are checked and a set of feasible treatment options is determined, wherein for each of the feasible treatment options the dentition is meeting the feasibility requirements assigned to the respective feasible treatment option, wherein the treatment proposal comprises the set of feasible treatment options and identifies for each of the feasible treatment options of the set of feasible treatment options implementation parameters determined for the measures of the respective feasible treatment option.
19. The computer system of any of the previous items, the providing of the set of treatment options comprising providing as an output via a user interface of the computer system a predefined set of selectable treatment options, in response to the providing, receiving via the user interface as an input the set of treatment options comprising treatment options selected from set of selectable treatment options.
20. The computer system of item 19, the input furthermore comprising a definition of the ranking order of the selected treatment options.
21. A computer program product for providing a treatment proposal for a dentition of a patient, the computer program product comprising a computer readable storage medium having program instructions embodied therewith, the program instructions being executable by a processor of a computer system to cause the computer system to:
provide a 3D digital model of a current state of the dentition as a current state model using scan data of the dentition;
provide a 3D digital model of a target state of the dentition to be achieved as a target state model, the target state model being generated using the current state model;
provide a set of treatment options for treating the dentition,
each of the treatment options defining one or more pre-defined measures of dentition modifications,
each of the treatment options being assigned with a set of one or more feasibility requirements to be met by the dentition for the treatment option to be feasible; check one or more of the provided treatment options, wherein the checking comprises determining whether the dentition of the patient is meeting the feasibility requirements assigned to the treatment option being checked using the current state model;

in case the dentition is determined to meet the feasibility requirements assigned to the treatment option being checked, provide the treatment proposal identifying the respective treatment option and implementation parameters determined for the measures of the identified treatment option for modifying the current state model such that one or more discrepancies of the current state model relative to the target state model are compensated.

22. A computer-implemented method for providing a treatment proposal for a dentition of a patient, the method comprising:

providing a 3D digital model of a current state of the dentition as a current state model using scan data of the dentition;

providing a 3D digital model of a target state of the dentition to be achieved as a target state model, the target state model being generated using the current state model;

providing a set of treatment options for treating the dentition, each of the treatment options defining one or more pre-defined measures of dentition modifications, each of the treatment options being assigned with a set of one or more feasibility requirements to be met by the dentition for the treatment option to be feasible; checking one or more of the provided treatment options, wherein the checking comprises determining whether the dentition of the patient is meeting the feasibility requirements assigned to the treatment option being checked using the current state model;

in case the dentition is determined to meet the feasibility requirements assigned to the treatment option being checked, providing the treatment proposal identifying the respective treatment option and implementation parameters determined for the measures of the identified treatment option for modifying the current state model such that one or more discrepancies of the current state model relative to the target state model are compensated.

LIST OF REFERENCE NUMERALS 10 computer system
11 system
14 external device
16 processing unit
18 bus
20 network adapter
22 I/O interface
24 display
28 memory
30 RAM
32 cache
34 storage system
40 program
42 program module
50 graphical user interface
52 control elements
54 hardware device
56 keyboard
58 mouse
60 3D printing device
62 printing element
70 machining device
72 machining tool
74 holding device
76 blank
78 raw material
100 crown
102 external surface
104 bonding surface
106 clearance
120 set of treatment options
122 treatment options
124 treatment proposal
126 treatment instructions

The invention claimed is:

1. A computer system for providing a treatment proposal for a dentition of a patient, the computer system comprising a processor and a memory storing program instructions executable by the processor, wherein execution of the program instructions by the processor causes the computer system to:

provide a three-dimensional (3D) digital model of a current state of the dentition as a current state model using scan data of the dentition;

provide a 3D digital model of a target state of the dentition to be achieved as a target state model, the target state model being generated using the current state model;

provide a set of treatment options for treating the dentition, each of the treatment options defining one or more pre-defined measures of dentition modifications, each of the treatment options being assigned with a set of one or more feasibility requirements to be met by the dentition for the treatment option to be feasible;

the set of treatment options comprising using dental prostheses and one or more of: using one or more veneers of the dental prostheses to be arranged on one or more teeth of the dentition as measures of dentition modifications; and using one or more crowns of the dental prostheses to be arranged on one or more teeth or tooth stumps of the dentition as the measures of the dentition modifications;

check the provided treatment options of using the one or more veneers and of using the one or more crowns by:

determining whether the dentition of the patient is meeting the feasibility requirements assigned to the treatment option being checked using the current state model, the determining comprising:

determining whether the dentition meets the feasibility requirements assigned to the treatment option of using the one or more veneers, the assigned feasibility requirements being checked for the treatment option of using the one or more veneers comprising: sufficient support by the teeth or tooth stumps for the one or more veneers, and an absence of contraindication; and in response to the dentition being determined to not meet the feasibility requirements assigned to the treatment option of using the one or more veneers, determining whether the dentition meets the feasibility requirements assigned to the treatment option of using crowns; the determining whether the dentition meets the feasibility requirements assigned to the treatment option of using crowns comprising:

determining of implementation parameters for the one or more crowns comprising generating 3D digital models of the one or more crowns; the 3D digital models of the one or more crowns being configured to match outer forms of crowns of one or more teeth of the 3D digital model of a target state of the dentition; and checking that a material thickness of the one or more crowns defined by the 3D digital models of the one or more crowns is equal to or larger than a predefined minimum thickness;

in response to the dentition being determined to meet the feasibility requirements assigned to the treatment option of using the one or more crowns, provide the treatment proposal identifying the respective treatment option and the implementation parameters determined for the measures of the identified treatment option for modifying the current state model such that one or more discrepancies of the current state model relative to the target state model are compensated;

provide control data configured to control a manufacturing of the one or more crowns using a manufacturing device, the control data comprising the implementation parameters with the generated 3D digital models of the one or more crowns as templates for the manufacturing of the one or more crowns; and manufacture the one or more crowns using the manufacturing device, wherein the manufacturing device is controlled using the control data, wherein the one or more manufactured crowns are physical copies of the 3D digital models of the one or more crowns.

2. The computer system of claim 1, wherein one or more of the feasibility requirements depend on the implementation parameters of the measures of the treatment option, wherein the determining whether the dentition of the patient is meeting the feasibility requirements assigned to the treatment option being checked is further based on the implementation parameters determined for the treatment option being checked.

3. The computer system of claim 1, wherein the providing of the current state model comprises generating the current state model using the scan data.

4. The computer system of claim 1, wherein the generating of the target state model comprises replacing one or more 3D digital models of actual teeth or tooth stumps comprised by the current state model with one or more 3D digital models of teeth from a tooth library.

5. The computer system of claim 1, wherein the generating of the target state model comprises modifying one or more features of the following features of one or more 3D digital models of actual teeth or tooth stumps comprised by the current state model: shape, size, orientation.

6. The computer system of claim 1, wherein the set of treatment options further comprises:
replacing one or more teeth or tooth stumps of the dentition as measures of dentition modification,
wherein the replacing comprises extracting the one or more teeth from the dentition and inserting one or more dental implants configured for supporting a crown or a bridge.

7. The computer system of claim 6, wherein one or more of the treatment options further comprises preparing the teeth for the dental prostheses, wherein the preparing comprises removing tooth substance to shape a support surface configured for supporting the dental prosthesis.

8. The computer system of claim 7, wherein the implementation parameters for one or more of the measures of the treatment options comprises determining one or more sections of teeth comprising the tooth substance.

9. The computer system of claim 1, wherein the implementation parameters for one or more of the measures of the treatment options comprises determining one or more of the following: a size of the dental prostheses, and a shape of the dental prostheses.

10. The computer system of claim 1, wherein the feasibility requirements comprises one or more of the following requirements: sufficient wall thickness of the dental prostheses used as measures of the treatment option, and sufficient dimensions of the teeth or tooth stumps for enabling a preparation for the dental prostheses used as measures of the treatment option, absence of contraindication.

11. The computer system of claim 10, wherein the contraindications comprises one or more of the following: bruxism, tooth damage.

12. The computer system of claim 10, wherein additional scan data is provided for checking the feasibility requirements.

13. The computer system of claim 1, wherein the treatment options are ordered according to a ranking order, the provided treatment options being checked subsequently following the ranking order, until the dentition is determined to meet the feasibility requirements assigned to the treatment option being checked, in case the dentition is determined to meet the feasibility requirements assigned to the treatment option being checked, the checking being interrupted.

14. The computer system of claim 13, wherein, upon receiving a continuation command via a user interface, the checking is continued with a next treatment option following the ranking order.

15. The computer system of claim 13, wherein the interruption of the checking causes a terminating of the checking.

16. The computer system of claim 1, wherein all of the treatment options of the set of treatment options are checked and a set of feasible treatment options is determined, wherein for each of the feasible treatment options the dentition is meeting the feasibility requirements assigned to the respective feasible treatment option, wherein the treatment proposal comprises the set of feasible treatment options and identifies for each of the feasible treatment options of the set of feasible treatment options implementation parameters determined for the measures of the respective feasible treatment option.

17. The computer system of claim 16, wherein execution of the program instructions by the processor further causes the computer system to receive input comprising a definition of a ranking order of the selected treatment options.

18. The computer system of claim 1, wherein the providing of the set of treatment options comprises providing as an output via a user interface of the computer system a predefined set of selectable treatment options, in response to the providing, receiving via the user interface as an input the set of treatment options comprising treatment options selected from the set of selectable treatment options.

19. The computer system of claim 1, wherein the set of treatment options further comprises using orthodontics.

20. A non-transitory computer program product for providing a treatment proposal for a dentition of a patient, the computer program product comprising a computer readable storage medium having program instructions embodied therewith, the program instructions being executable by a processor of a computer system to cause the computer system to:
provide a three-dimensional (3D) digital model of a current state of the dentition as a current state model using scan data of the dentition;

provide a 3D digital model of a target state of the dentition to be achieved as a target state model, the target state model being generated using the current state model;
provide a set of treatment options for treating the dentition,
    each of the treatment options defining one or more pre-defined measures of dentition modifications,
    each of the treatment options being assigned with a set of one or more feasibility requirements to be met by the dentition for the treatment option to be feasible;
    the set of treatment options comprising using dental prostheses and one or more of: using one or more veneers of the dental prostheses to be arranged on one or more teeth of the dentition as measures of dentition modifications; and using one or more crowns of the dental prostheses to be arranged on one or more teeth or tooth stumps of the dentition as the measures of the dentition modifications;
check the provided treatment options of using the one or more veneers and of using the one or more crowns by:
determining whether the dentition of the patient is meeting the feasibility requirements assigned to the treatment option being checked using the current state model, the determining comprising:
    determining whether the dentition meets the feasibility requirements assigned to the treatment option of using the one or more veneers, the assigned feasibility requirements being checked for the treatment option of using the one or more veneers comprising: sufficient support by the teeth or tooth stumps for the one or more veneers, and an absence of contraindication; and
    in response to the dentition being determined to not meet the feasibility requirements assigned to the treatment option of using the one or more veneers, determining whether the dentition meets the feasibility requirements assigned to the treatment option of using crowns; the determining whether the dentition meets the feasibility requirements assigned to the treatment option of using crowns comprising:
        determining of implementation parameters for the one or more crowns comprising generating 3D digital models of the one or more crowns; the 3D digital models of the one or more crowns being configured to match outer forms of crowns of one or more teeth of the 3D digital model of a target state of the dentition; and
        checking that a material thickness of the one or more crowns defined by the 3D digital models of the one or more crowns is equal to or larger than a predefined minimum thickness;
    in response to the dentition being determined to meet the feasibility requirements assigned to the treatment option of using the one or more crowns, provide the treatment proposal identifying the respective treatment option and the implementation parameters determined for the measures of the identified treatment option for modifying the current state model such that one or more discrepancies of the current state model relative to the target state model are compensated;
provide control data configured to control a manufacturing of the one or more crowns using a manufacturing device, the control data comprising the implementation parameters with the generated 3D digital models of the one or more crowns as templates for the manufacturing of the one or more crowns; and
manufacture the one or more crowns using the manufacturing device, wherein the manufacturing device is controlled using the control data, wherein the one or more manufactured crowns are physical copies of the 3D digital models of the one or more crowns.

21. A computer-implemented method for providing a treatment proposal for a dentition of a patient, the method comprising:
providing a three-dimensional (3D) digital model of a current state of the dentition as a current state model using scan data of the dentition;
providing a 3D digital model of a target state of the dentition to be achieved as a target state model, the target state model being generated using the current state model;
providing a set of treatment options for treating the dentition,
    each of the treatment options defining one or more pre-defined measures of dentition modifications,
    each of the treatment options being assigned with a set of one or more feasibility requirements to be met by the dentition for the treatment option to be feasible;
    the set of treatment options comprising using dental prostheses and one or more of: using one or more veneers of the dental prostheses to be arranged on one or more teeth of the dentition as measures of dentition modifications; and using one or more crowns of the dental prostheses to be arranged on one or more teeth or tooth stumps of the dentition as the measures of the dentition modifications;
checking the provided treatment options of using the one or more veneers and of using the one or more crowns by: determining whether the dentition of the patient is meeting the feasibility requirements assigned to the treatment option being checked using the current state model, the determining comprising:
    determining whether the dentition meets the feasibility requirements assigned to the treatment option of using the one or more veneers, the assigned feasibility requirements being checked for the treatment option of using the one or more veneers comprising: sufficient support by the teeth or tooth stumps for the one or more veneers, and an absence of contraindication; and
    in response to the dentition being determined to not meet the feasibility requirements assigned to the treatment option of using the one or more veneers, determining whether the dentition meets the feasibility requirements assigned to the treatment option of using crowns; the determining whether the dentition meets the feasibility requirements assigned to the treatment option of using crowns comprising:
        determining of implementation parameters for the one or more crowns comprising generating 3D digital models of the one or more crowns; the 3D digital models of the one or more crowns being configured to match outer forms of crowns of one or more teeth of the 3D digital model of a target state of the dentition; and
        checking that a material thickness of the one or more crowns defined by the 3D digital models of the one or more crowns is equal to or larger than a predefined minimum thickness;
    in response to the dentition being determined to meet the feasibility requirements assigned to the treatment option of using the one or more crowns, providing the treatment proposal identifying the respective treatment option and the implementation parameters determined for the measures of the identified treatment option for modifying the current state model such that one or more discrepancies of the current state model relative to the target state model are compensated;

providing control data configured to control a manufacturing of the one or more crowns using a manufacturing device, the control data comprising the implementation parameters with the generated 3D digital models of the one or more crowns as templates for the manufacturing of the one or more crowns; and manufacturing the one or more crowns using the manufacturing device, wherein the manufacturing device is controlled using the control data, wherein the one or more manufactured crowns are physical copies of the 3D digital models of the one or more crowns.

\* \* \* \* \*